(12) United States Patent
Kato et al.

(10) Patent No.: US 7,691,881 B2
(45) Date of Patent: Apr. 6, 2010

(54) 1-ISOPROPYL-2-OXO-1,2-DIHYDROPYRIDINE-3-CARBOXAMIDE DERIVATIVES HAVING 5-HT$_4$ RECEPTOR AGONISTIC ACTIVITY

(75) Inventors: Tomoki Kato, Chita-gun (JP); Kiyoshi Kawamura, Chita-gun (JP); Chikara Uchida, Chita-gun (JP)

(73) Assignee: Pfizer Inc, New York, NY (US)

( * ) Notice: Subject to any disclaimer, the term of this patent is extended or adjusted under 35 U.S.C. 154(b) by 884 days.

(21) Appl. No.: 10/597,480

(22) PCT Filed: Jan. 18, 2005

(86) PCT No.: PCT/IB2005/000173

§ 371 (c)(1), (2), (4) Date: Jul. 27, 2006

(87) PCT Pub. No.: WO2005/073222

PCT Pub. Date: Aug. 11, 2005

(65) Prior Publication Data

US 2008/0293767 A1    Nov. 27, 2008

Related U.S. Application Data

(60) Provisional application No. 60/540,143, filed on Jan. 29, 2004.

(51) Int. Cl.
A61K 31/445 (2006.01)
C07D 401/12 (2006.01)

(52) U.S. Cl. .................... 514/318; 514/235.5; 514/255; 546/139; 546/208; 546/193

(58) Field of Classification Search ............... 514/318, 514/235.5, 255; 546/139, 208, 193
See application file for complete search history.

(56) References Cited

U.S. PATENT DOCUMENTS 5,696,129 A    12/1997    King et al. ............... 514/291

6,979,690 B2 *   12/2005   Gymer et al. ............... 514/318
2003/0207875 A1   11/2003   Gymer et al. ............... 514/227.8

FOREIGN PATENT DOCUMENTS

WO    WO 9902494    1/1999

OTHER PUBLICATIONS

International Search Report for Appln. PCT/IB2005/000173.

* cited by examiner

*Primary Examiner*—Celia Chang
(74) *Attorney, Agent, or Firm*—Gregg C. Benson; James T. Jones

(57) ABSTRACT

This invention provides a compound of formula (I): wherein R$^1$ represents an alkyl group having from 1 to 4 carbon atoms or a halogen atom, R$^2$ represents an alkyl group having from 1 to 4 carbon atoms, R$^3$ represents a hydrogen atom or a hydroxy group, and A represents an oxygen atom or a group of the formula —C(R$^4$)(R$^5$)— (in which R$^4$ represents a hydrogen atom or an alkyl group having from 1 to 4 carbon atoms and R$^5$ represents a hydroxy group or an alkoxy group having from 1 to 4 carbon atoms) or a pharmaceutically acceptable salts thereof. These compounds have 5-HT$_4$ receptor agonistic activity, and thus are useful for the treatment of gastroesophageal reflux disease, non-ulcer dyspepsia, functional dyspepsia, irritable bowel syndrome or the like in mammalian, especially humans.

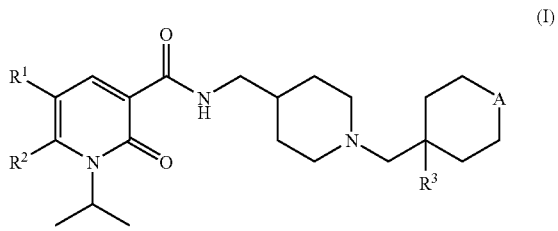

(I)

11 Claims, No Drawings

1-ISOPROPYL-2-OXO-1,2-DIHYDROPYRIDINE-3-CARBOXAMIDE DERIVATIVES HAVING 5-HT$_4$ RECEPTOR AGONISTIC ACTIVITY

The present application is a national stage of PCT/IB2005/000173 and claims priority of U.S. Appln. No. 60/540,143, filed 29 Jan. 2004.

TECHNICAL FIELD

This invention relates to novel 1-isopropyl-2-oxo-1,2-dihydropyridine-3-carboxamide derivatives. These compounds have selective 5-HT$_4$ receptor agonistic activity. The present invention also relates to a pharmaceutical composition, a method of treatment and a use, comprising the above derivatives for the treatment of disease conditions mediated by 5-HT$_4$ receptor activity.

BACKGROUND ART

In general, 5-HT$_4$ receptor agonists are found to be useful for the treatment of a variety of diseases such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive disorder, emesis, migraine, neurological disease, pain, cardiovascular disorders such as cardiac failure and heart arrhythmia, and apnea syndrome (See *TiPs*, 1992, 13, 141; Ford A. P. D. W. et al., *Med. Res. Rev.*, 1993, 13, 633; Gullikson G. W. et al., *Drug Dev. Res.*, 1992, 26, 405; Richard M. Eglen et al, *TiPS*, 1995, 16, 391; Bockaert J. Et al., *CNS Drugs*, 1, 6; Romanelli M. N. et al., *Arzheim Forsch./Drug Res.*, 1993, 43, 913; Kaumann A. et al., *Naunyn-Schmiedeberg's*. 1991, 344, 150; and Romanelli M. N. et al., *Arzheim Forsch./Drug Res.*, 1993, 43, 913).

WO2003/57688 discloses 1-alkyl-2-oxo-1,2-dihydropyridine-3-carboxamide derivatives as 5-HT$_4$ receptor modulators. Especially, the compound represented by the following formula is disclosed in Example 4:

Compound A

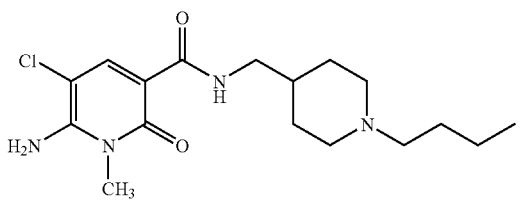

However, this compound shows weak affinity to 5-HT$_4$ receptor and low permeability against caco2 membrane.

Therefore, it was desired to find out 5-HT$_4$ receptor agonists which show stronger 5HT$_4$ receptor agonistic activities and better permeability against caco2 membrane in order to reduce side effects.

BRIEF DISCLOSURE OF THE INVENTION

In this invention, we found out that (1) replacing the amino group with an alkyl group, especially, methyl or ethyl group, at 6-position much improved the permeability against caco2 membrane whilst retaining affinity to 5-HT$_4$ receptor and (2) replacing the methyl group with isopropyl group at 1-position improved 5HT$_4$ receptor agonistic activities.

Therefore, it has now surprisingly been found that compounds of this invention have stronger selective 5-HT$_4$ agonistic activity with improved caco2 permeability, compared with the prior arts, and thus are useful for the treatment of disease conditions mediated by 5-HT$_4$ activity such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive disorder, emesis, migraine, neurological disease, pain, and cardiovascular disorders such as cardiac failure and heart arrhythmia, diabetes and apnea syndrome (especially caused by an opioid administration).

The compounds of the present invention may show less toxicity, good absorption, distribution, good solubility, low protein binding affinity, less drug-drug interaction, and good metabolic stability.

The present invention provides compounds of the following formula (I) or pharmaceutically acceptable salts thereof.

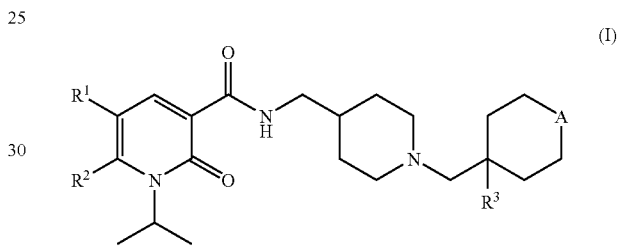

(I)

wherein

R$^1$ represents an alkyl group having from 1 to 4 carbon atoms or a halogen atom, R$^2$ represents an alkyl group having from 1 to 4 carbon atoms, R$^3$ represents a hydrogen atom or a hydroxy group, and A represents an oxygen atom or a group of the formula —C(R$^4$)(R$^5$)— (in which R$^4$ represents a hydrogen atom or an alkyl group having from 1 to 4 carbon atoms and R$^5$ represents a hydroxy group or an alkoxy group having from 1 to 4 carbon atoms).

Also, the present invention provides the use of a compound of formula (I) or its pharmaceutically acceptable salt, for the manufacture of a medicament for the treatment of a condition mediated by 5-HT$_4$ receptor activity.

Preferably, the present invention also provides the use of a compound of formula (I) or its pharmaceutically acceptable salt, for the manufacture of a medicament for the treatment of diseases selected from gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive disorder, emesis, migraine, neurological disease, pain, and cardiovascular disorders such as cardiac failure and heart arrhythmia, diabetes and apnea syndrome.

Also, the present invention provides a pharmaceutical composition comprising a compound of formula (I) or its pharmaceutically acceptable salt together with a pharmaceutically acceptable carrier for said compound.

Further, the present invention provides a method for the treatment of a condition mediated by 5-HT$_4$ receptor activity, in a mammalian subject, which comprises administering to a mammal in need of such treatment a therapeutically effective amount of a compound of formula (I) or its pharmaceutically acceptable salt.

Preferably, the present invention provides a method for the treatment of diseases selected from gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageal disease, nausea, central nervous system disease, Alzheimer's disease, cognitive disorder, emesis, migraine, neurological disease, pain, and cardiovascular disorders such as cardiac failure and heart arrhythmia, diabetes and apnea syndrome.

DETAILED DESCRIPTION OF THE INVENTION

In the compounds of the present invention,

Where $R^1$ represents an alkyl group having from 1 to 4 carbon atoms, $R^2$ represents an alkyl group having from 1 to 4 carbon atoms, and $R^4$ represents an alkyl group having from 1 to 4 carbon atoms, this may be a straight or branched chain group, and examples include the methyl, ethyl, propyl isopropyl, butyl, isobutyl, sec-butyl and t-butylyl. Of these, we prefer those alkyl groups having from 1 to 3 carbon atoms, preferably the methyl, ethyl, propyl and isopropyl, and most preferably the methyl and ethyl groups.

Where $R^1$ represents a halogen atom, this may be a fluorine, chlorine, bromine or iodine atom. Of these, we prefer fluoro or chloro.

Where $R^5$ represents an alkoxy group having from 1 to 4 carbon atoms, this represents the oxy group which is substituted by an alkyl group having from 1 to 4 carbon atoms defined above and may be a straight or branched chain group, and examples include the methoxy, ethoxy, propoxy, isopropoxy, butoxy, isobutoxy, sec-butoxy and t-butoxy. Of these, we prefer those alkoxy groups having from 1 to 3 carbon atoms, preferably the methoxy, ethoxy, propoxy and isopropoxy, and most preferably the methoxy and ethoxy groups.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

Preferred classes of compounds of the present invention are those compounds of formula (I) and salts thereof in which:

(A) $R^1$ represents a halogen atom;

(B) $R^2$ represents an alkyl group having from 1 to 2 carbon atoms;

(C) $R^3$ represents a hydroxy group;

(D) A represents an oxygen atom.

Particularly preferred compounds of the present invention are those compounds of formula (I) and salts thereof in which (E) $R^1$ represents a halogen atom, $R^2$ represents an alkyl group having from 1 to 4 carbon atoms, $R^3$ represents a hydrogen atom or a hydroxy group, and A represents an oxygen atom or a group of the formula —C($R^4$)($R^5$)— (in which $R^4$ represents a hydrogen atom or an alkyl group having from 1 to 4 carbon atoms and $R^5$ represents a hydroxy group or an alkoxy group having from 1 to 4 carbon atoms);

(F) $R^1$ represents an alkyl group having from 1 to 4 carbon atoms or a halogen atom, $R^2$ represents an alkyl group having from 1 to 2 carbon atoms, $R^3$ represents a hydrogen atom or a hydroxy group, and A represents an oxygen atom or a group of the formula —C($R^4$)($R^5$)— (in which $R^4$ represents a hydrogen atom or an alkyl group having from 1 to 4 carbon atoms and $R^5$ represents a hydroxy group or an alkoxy group having from 1 to 4 carbon atoms);

(G) $R^1$ represents an alkyl group having from 1 to 4 carbon atoms or a halogen atom, $R^2$ represents an alkyl group having from 1 to 4 carbon atoms, $R^3$ represents a hydroxy group, and A represents an oxygen atom or a group of the formula —C($R^4$)($R^5$)— (in which $R^4$ represents a hydrogen atom or an alkyl group having from 1 to 4 carbon atoms and $R^5$ represents a hydroxy group or an alkoxy group having from 1 to 4 carbon atoms);

(H) $R^1$ represents an alkyl group having from 1 to 4 carbon atoms or a halogen atom, $R^2$ represents an alkyl group having from 1 to 4 carbon atoms, $R^3$ represents a hydrogen atom or a hydroxy group, and A represents an oxygen atom.

The more preferred classes of compounds of the present invention are those in which:

(I) $R^1$ represents a halogen atom, $R^2$ represents an alkyl group having from 1 to 2 carbon atoms, $R^3$ represents a hydrogen atom or a hydroxy group, and A represents an oxygen atom or a group of the formula —C($R^4$)($R^5$)— (in which $R^4$ represents a hydrogen atom or an alkyl group having from 1 to 4 carbon atoms and $R^5$ represents a hydroxy group or an alkoxy group having from 1 to 4 carbon atoms);

(J) $R^1$ represents an alkyl group having from 1 to 4 carbon atoms or a halogen atom, $R^2$ represents an alkyl group having from 1 to 4 carbon atoms, $R^3$ represents a hydroxy group, and A represents an oxygen;

(K) $R^1$ represents a halogen atom, $R^2$ represents an alkyl group having from 1 to 2 carbon atoms, $R^3$ represents hydroxy group, and A represents an oxygen atom or a group of the formula —C($R^4$)($R^5$)— (in which $R^4$ represents a hydrogen atom or an alkyl group having from 1 to 4 carbon atoms and $R^5$ represents a hydroxy group or an alkoxy group having from 1 to 4 carbon atoms);

(L) $R^1$ represents a halogen atom, $R^2$ represents an alkyl group having from 1 to 4 carbon atoms, $R^3$ represents a hydroxy group, and A represents an oxygen;

(M) $R^1$ represents a halogen atom, $R^2$ represents an alkyl group having from 1 to 2 carbon atoms, $R^3$ represents a hydroxy group, and A represents an oxygen;

The most preferred individual compounds of the present invention are 5-chloro-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide;

5-chloro-6-ethyl-N-({1-[(4-hydroxytetrahydro-2H-pyran-4-yl)methyl]piperidin-4-yl}methyl)-1-isopropyl-2-oxo-1,2-dihydropyridine-3-carboxamide;

N-({1-[(4-hydroxytetrahydro-2H-pyran-4-yl)methyl]piperidin-4-yl}methyl)-1-isopropyl-5,6-dimethyl-2-oxo-1,2-dihydropyridine-3-carboxamide;

5-bromo-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide;

5-fluoro-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide;

5-chloro-N-{[1-(cyclohexylmethyl)piperidin-4-yl]methyl}-1-isopropyl-6-methyl-2-oxo-1,2-dihydropyridine-3-carboxamide;

5-chloro-N-({1-[(1-hydroxycyclohexyl)methyl]piperidin-4-yl}methyl)-1-isopropyl-6-methyl-2-oxo-1,2-dihydropyridine-3-carboxamide;

or a pharmaceutically acceptable salt thereof.

The compounds of the present invention can exist in the form of various stereoisomers, R and S isomers, depending upon the presence of asymmetric carbon atoms. The present invention covers both the individual isomers and mixtures thereof, including racemic mixtures.

The compounds of the invention may take up water upon exposure to the atmosphere to absorb water or to produce a hydrate. The present invention covers such hydrates. Additionally, certain other solvents may be taken up by the compounds of the present invention to produce solvates, which also form part of the present invention.

The compounds of the present invention can form salts. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with methylamine, dimethylamine, triethylamine, diisopropylamine, cyclohexylamine or dicyclohexylamine; and salts with a basic amino acid, such as lysine or arginine.

General Synthesis

The compounds of the present invention may be prepared by a variety of processes well known for the preparation of compounds of this type, for example as shown in the following Methods A to E The following Methods A, C and D illustrate the preparation of compounds of formula (I).

Unless otherwise indicated, $R^1$, $R^2$, $R^3$, $R^4$, $R^5$ and A in the following Methods are defined as above. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1999). All starting materials in the following general syntheses may be commercially available or obtained by conventional methods known to those skilled in the art.

Method A

This illustrates the preparation of compounds of formula (Ia) wherein $R^1$ is a halogen atom.

Reaction Scheme A

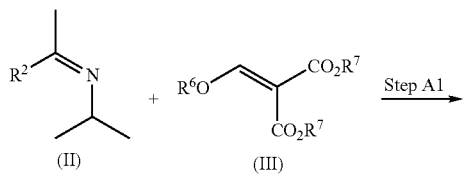

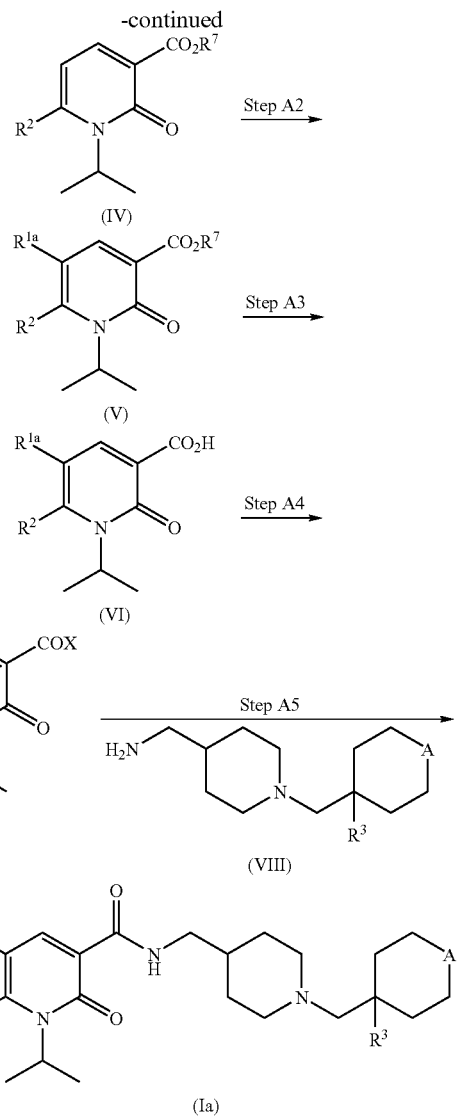

In the above formulae, $R^{1a}$ represents a halogen atom; X represents a chlorine or bromine atom; and each of $R^6$ and $R^7$ represents an alkyl group having 1 to 4 carbon atoms.

Step A1

In this step, the pyridone compound (IV) is prepared by the condensation of the eneamine compound (II) with the enol ether compound (III) in an inert solvent.

The reaction is normally and preferably effected in the presence of solvent. There is no particular restriction on the nature of the solvent to be employed, provided that it has no adverse effect on the reaction or the materials involved and that it can dissolve the starting materials, at least to some extent. Examples of suitable solvents include: aromatic hydrocarbons, such as benzene, toluene and xylene; and ethers such as diisopropyl ether, diphenyl ether, tetrahydrofuran and dioxane. Of these solvents, we prefer aromatic hydrocarbons.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 50° C. to 250° C., more preferably from 120° C. to 200 C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 60 minutes to 12 hours, will usually suffice.

Step A2

In this step, the compound of the formula (V) is prepared by the halogenating the pyridon compound (IV) prepared as described in Step A1.

Examples of suitable halogenating agents include: fluorinating agents, such as xenon difluoride; chlorinating agents, such as chlorine, sulfuryl chloride or N-chlorosuccinimide; brominating agents, such as bromine or N-bromosuccinimide; and iodinating agents, such as iodine or N-iodosuccinimide. The reaction may be carried out according to the methods described in detail in "The Chemistry of Heterocyclic Compounds", Vol 48, Part 1, p 348-395, published by John Wiley & Sons.

The reaction is normally and preferably effected in the presence of solvent. There is no particular restriction on the nature of the solvent to be employed, provided that it has no adverse effect on the reaction or the materials involved and that it can dissolve the starting materials, at least to some extent. Examples of suitable solvents include: halogenated hydrocarbons, such as dichloromethane, chloroform, carbon tetrachloride and 1,2-dichloroethane; amides, such as N,N-dimethylformamide and N,N-dimethylacetamide; and ethers such as diisopropyl ether, diphenyl ether tetrahydrofuran and dioxane. Of these solvents, we prefer: halogenated hydrocarbons.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 120 C, more preferably from 20 C to 80 C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 12 hours to 24 hours, will usually suffice.

Step A3

In this step, the compound of formula (V) is prepared by hydrolyzing the ester portion of the compound of formula (IV) prepared as described in Step A2.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: alcohols, such as methanol, ethanol, propanol, 2-propanol and butanol; water; and ethers such as diisopropyl ether, diphenyl ether tetrahydrofuran and dioxane. Of these solvents, we prefer alcohols.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide. Of these, we prefer sodium hydroxide or potassium hydroxide. The quantity of the base required for the reaction may also vary widely, depending on many factors, notably the reaction temperature and the nature of the starting materials and solvent employed. However, that the reaction is effected under the preferred conditions, the quantity of the base as chemical equivalent to the starting material from 2 to 5, will usually suffice.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 120° C., more preferably from 20° C. to 80° C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 60 minutes to 12 hours, will usually suffice.

Step A4

In this step, the compound of formula (VII) is prepared by forming the acyl halide from the carboxylic portion of the compound of formula (V) prepared as described in Step A3.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane. Of these solvents, we prefer 1,2-dichloroethane.

Examples of suitable reagents include: chlorinating agents, such as oxalyl chloride or thionyl chloride; and brominating agents, such as thionyl bromide. The quantity of the reagent required for the reaction may also vary widely, depending on many factors, notably the reaction temperature and the nature of the starting materials and solvent employed. However, that the reaction is effected under the preferred conditions, the quantity of the reagent as chemical equivalent to the starting material from 2 to 5, will usually suffice.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 100° C., more preferably from 0° C. to 40° C. The time required for the reaction may also vary widely, depending on many factors, notably the reaction temperature and the nature of the starting materials and solvent employed. However, provided that the reaction is effected under the preferred conditions outlined above, a period of from 5 minutes to 10 hours, more preferably from 60 minutes to 5 hours, will usually suffice.

Step A5

In this step, the desired compound of formula (Ia) of the present invention is prepared by forming the amide from the compound of formula (VI) prepared as described in Step A4 and the amine compound of formula (VIII).

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane. Of these solvents, we prefer dichloromethane or 1,2-dichloroethane.

The reaction is carried out in the presence of a base. There is likewise no particular restriction on the nature of the bases used, and any base commonly used in reactions of this type may equally be used here. Examples of such bases include: amines, such as triethylamine, diisopropylethylamine, tributylamine, pyridine, picoline and 4-(N,N-dimethylamino)pyridine. Of these, we prefer triethylamine, diisopropylethylamine or pyridine. The quantity of the base required for the reaction may also vary widely, depending on many factors, notably the reaction temperature and the nature of the starting materials and solvent employed. However, that the reaction is effected under the preferred conditions, the quantity of the base as chemical equivalent to the starting material from 1 to 4, more preferably from 1 to 1.4, will usually suffice.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 100° C., more preferably from 0° C. to 50° C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 3 hours to 18 hours, will usually suffice.

Method B

This illustrates the alternative preparation of the compound of formula (V) wherein $R^1$ is a halogen atom; and $R^2$ is an alkyl group having 2 to 4 carbon atoms.

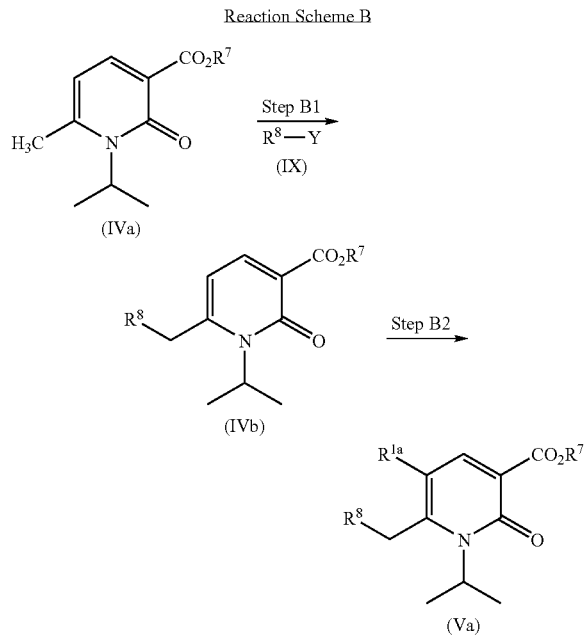

Reaction Scheme B

In the above formulae, $R^{1a}$ and $R^7$ are as defined above; $R^8$ represents an alkyl group having 1 to 3 carbon atoms; and Y represents a halogen atom.

Step B1

In this step, the compound of formula (VIb) is prepared by the alkylation of the compound of formula (IVa) with the compound of formula (IX) in the presence of a base.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane. Of these solvents, we prefer tetrahydrofuran.

There is likewise no particular restriction on the nature of the bases used, and any base commonly used in reactions of this type may equally be used here. Examples of such bases include: alkali metal amides, such as lithium diisopropyl amide, potassium diisopropyl amide, sodium diisopropyl amide, lithium bis(trimethylsilyl)amide and potassium bis(trimethylsilyl)amide. Of these, we prefer lithium diisopropyl amide or lithium bis(trimethylsilyl)amide. The quantity of the base required for the reaction may also vary widely, depending on many factors, notably the reaction temperature and the nature of the starting materials and solvent employed. However, that the reaction is effected under the preferred conditions, the quantity of the base as chemical equivalent to the starting material from 1 to 4, more preferably from 1 to 1.4, will usually suffice.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 120° C., more preferably from 20° C. to 80° C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 60 minutes to 12 hours, will usually suffice.

Step B2

In this step, the compound of formula (Va) is prepared by the halogenating the compound of formula (IVa) prepared as described in Step B1. The reaction may be carried out under the same conditions as described in Step A2 of Method A.

Method C

This illustrates the preparation of the desired compound of formula (Ib) wherein $R^1$ is an alkyl group having 1 to 4 carbon atoms.

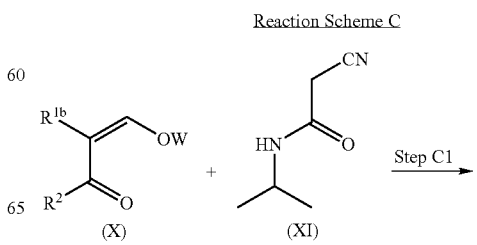

Reaction Scheme C

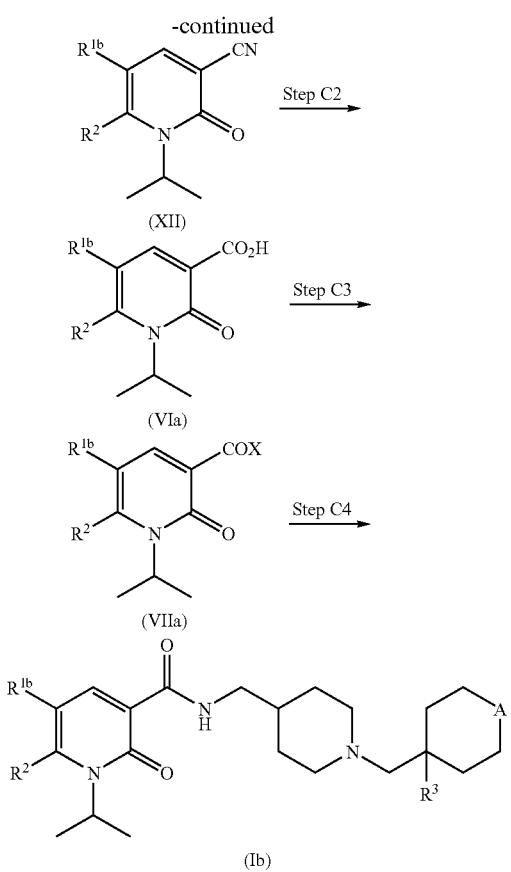

In the above formulae, X is as defined above; $R^{1b}$ represents an alkyl group having 1 to 4 carbon atoms; and W represents a hydrogen atom or an alkali metal atom, such as lithium, sodium or potassium.

Step C1

In this step, the compound of formula (XII) is prepared by the condensation of the compound of formula (X) with the compound of formula (XI) under the presence of an acid in an inert solvent.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: amides, such as N,N-dimethylformamide and N,N-dimethylacetamide; and Of these solvents, we prefer N,N-dimethylformamide.

There is likewise no particular restriction on the nature of the acids used, and any base commonly used in reactions of this type may equally be used here. Examples of such acids include: carboxylic acids, such as acetic acid, propionic acid or benzoic acid. Of these acids, we prefer acetic acid. The quantity of the acid required for the reaction may also vary widely, depending on many factors, notably the reaction temperature and the nature of the starting materials and solvent employed. However, that the reaction is effected under the preferred conditions, the quantity of the acid as chemical equivalent to the starting material from 1 to 4, more preferably 1 to 1.6, will usually suffice.

The reaction is carried out in the presence of a base. There is likewise no particular restriction on the nature of the bases used, and any base commonly used in reactions of this type may equally be used here. Examples of such bases include: amines, such as diethylamine, triethylamine, diisopropylethylamine, tributylamine, piperidine, pyridine, picoline and 4-(N,N-dimethylamino)pyridine. Of these, we prefer diethylamine or piperidine. The quantity of the base required for the reaction may also vary widely, depending on many factors, notably the reaction temperature and the nature of the starting materials and solvent employed. However, that the reaction is effected under the preferred conditions, the quantity of the base as chemical equivalent to the starting material from 0.01 to 1, more preferably 0.05 to 0.4, will usually suffice.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 100° C., more preferably from 0° C. to 50° C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 3 hours to 24 hours, will usually suffice.

Step C2

In this step, the compound of formula (VIa) is prepared by the hydrolysis of the compound of formula (XII) in an inert solvent.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; aromatic hydrocarbons, such as benzene, toluene and nitrobenzene; alcohols, such as methanol, ethanol, propanol, 2-propanol and butanol; and water. Of these solvents, we prefer the mixture of water and alcohols.

The reaction is carried out in the presence of a base. There is likewise no particular restriction on the nature of the bases used, and any base commonly used in reactions of this type may equally be used here. Examples of such bases include: alkali metal hydroxides, such as lithium hydroxide, sodium hydroxide and potassium hydroxide. Of these, we prefer sodium hydride or potassium hydroxide. The quantity of the base required for the reaction may also vary widely, depending on many factors, notably the reaction temperature and the nature of the starting materials and solvent employed. However, that the reaction is effected under the preferred conditions, the quantity of the base as chemical equivalent to the starting material from 1 to 5, will usually suffice.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 120° C., more preferably from 20° C. to 80° C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 60 minutes to 12 hours, will usually suffice.

Step C3

In this step, the compound of formula (VIIa) is prepared by forming acyl halide from carboxylic portion of the compound of formula (VIa) prepared as described in Step C2. The reaction may be carried out under the same conditions as described in Step A4 of Method A.

Step C4

In this step, the desired compound of formula (Ib) of the present invention is prepared by forming amide from the compound of formula (VIIa) prepared as described in Step C3. The reaction may be carried out under the same conditions as described in Step A5 of Method A.

Method D

This illustrates the alternative preparation of the desired compound of formula (Ic) and (Id).

Organic Synthesis, 494-653, (1999)], the disclosures of which are incorporated herein by reference. The following is a typical method, provided the protecting group is t-buthoxycarbonyl.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; and alcohols, such as methanol, ethanol, propanol, 2-propanol and butanol. Of these solvents, we prefer alcohols.

The reaction is carried out in the presence of excess amount of an acid. There is likewise no particular restriction on the

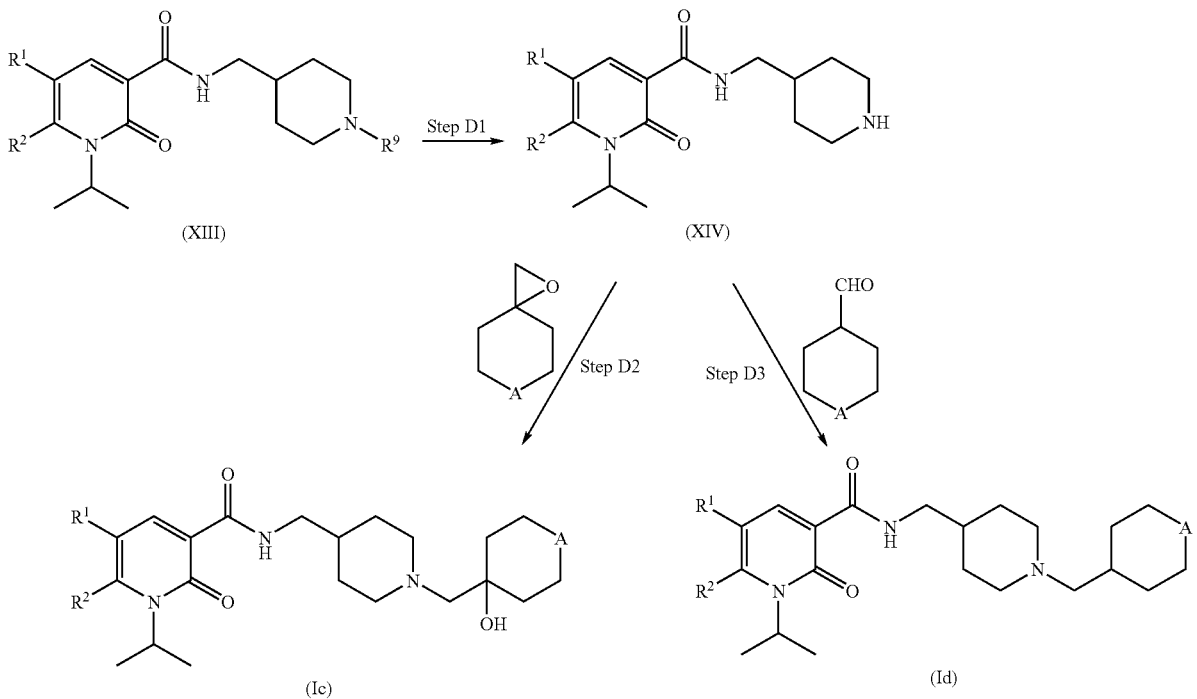

Reaction Scheme D

In the above formulae, $R^9$ represents an amino-protecting group.

The term "amino-protecting group", as used herein, signifies a protecting group capable of being cleaved by chemical means, such as hydrogenolysis, hydrolysis, electrolysis or photolysis and such amino protecting groups are described in Protective Groups in Organic Synthesis edited by T. W. Greene et al. (John Wiley & Sons, 1999). Typical amino protecting groups include benzyl, $C_2H_5O(C=O)-$, $CH_3(C=O)-$, t-butyldimethylsilyl, t-butyldiphenylsilyl, benzyloxycarbonyl and t-buthoxycarbonyl. Of these groups, we prefer t-buthoxycarbonyl.

Step D1

In this step, the piperidine compound (XIV) is prepared by the deprotection of the compound of formula (XIII) which may have been prepared, for example, as the same method as described in either Method A or Method C. This method is described in detail by T. W Greene et al. [Protective Groups in nature of the acids used, and any acid commonly used in reactions of this type may equally be used here. Examples of such acids include: acids, such as hydrochloric acid, or trifluoroacetic acid. Of these, we prefer hydrochloric acid.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 100° C., more preferably from 0° C. to 50° C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 3 hours to 24 hours, will usually suffice.

Step D2

In this step, the desired compound of formula (Ic) is prepared by the epoxy-opening substitution of the compound of formula (XIV) prepared as described in Step D1.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: ethers, such as diethyl ether, diisopropyl ether, tetrahydrofuran and dioxane; and alcohols, such as methanol, ethanol, propanol, 2-propanol and butanol. Of these solvents, we prefer alcohols.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from 0° C. to 120° C., more preferably from 20° C. to 80° C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 3 hours to 24 hours, will usually suffice.

Step D3

In this step, the desired compound of formula (Id) is prepared by the reductive amination of the compound of formula (XIV) prepared as described in Step D1.

The reaction is normally and preferably effected in the presence of solvent. There is no particular restriction on the nature of the solvent to be employed, provided that it has no adverse effect on the reaction or the reagents involved and that it can dissolve reagents, at least to some extent. Examples of suitable solvents include: halogenated hydrocarbons, such as dichloromethane, chloroform, carbon tetrachloride and 1,2-dichloroethane; ethers, such as diethyl ether, diisopropyl ether, dimethoxyethane, tetrahydrofuran and dioxane; alcohols, such as methanol, ethanol, propanol, 2-propanol and butanol; acetic acid; and water. Of these solvents, we prefer halogenated hydrocarbons.

The reaction is carried out in the presence of a reducing reagent. There is likewise no particular restriction on the nature of the reducing reagents used, and any reducing reagent commonly used in reactions of this type may equally be used here. Examples of such reducing reagent include: sodium borohydride, sodium cyanoborohydride and sodium triacetoxyborohydride. Of these, we prefer sodium triacetoxyborohydride. The quantity of the reducing reagent required for the reaction may also vary widely, depending on many factors, notably the reaction temperature and the nature of the starting materials and solvent employed. However, that the reaction is effected under the preferred conditions, the quantity of the reducing reagent as chemical equivalent to the starting material from 1 to 3, will usually suffice.

The reaction can take place over a wide range of temperatures, and the precise reaction temperature is not critical to the invention. The preferred reaction temperature will depend upon such factors as the nature of the solvent, and the starting materials. However, in general, we find it convenient to carry out the reaction at a temperature of from −20° C. to 60° C., more preferably from 0° C. to 50° C. The time required for the reaction may also vary widely, depending on many factors, notably the reaction temperature and the nature of the starting materials and solvent employed. However, provided that the reaction is effected under the preferred conditions outlined above, a period of from 5 minutes to 24 hours, more preferably from 1 hour to 12 hours, will usually suffice.

Method E

This illustrates the preparation of the compound of formula (VIII).

Reaction Scheme E

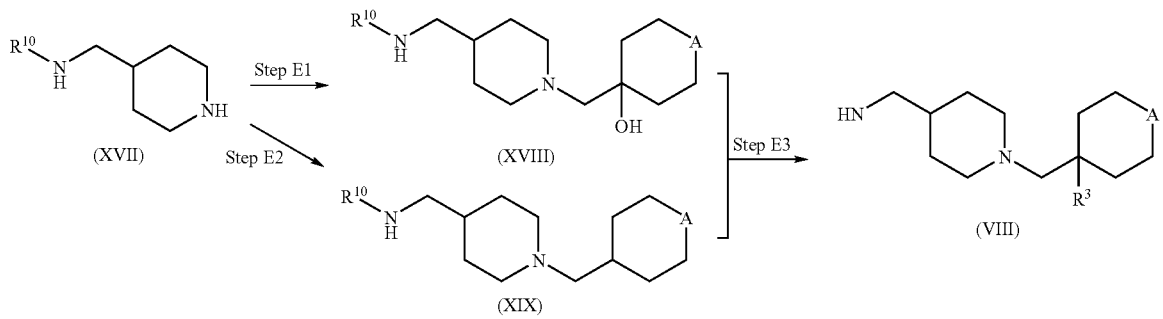

In the above formulae, $R^{10}$ represents an amino-protecting group.

Step E1

In this step, the compound of formula (XVIII) is prepared by the epoxy-opening substitution of the compound of formula (XVII). The reaction may be carried out under the same conditions as described in Step D2 of Method D.

Step E2

In this step, the compound of formula (XIX) is prepared by the reductive amination of the compound of formula (XVII). The reaction may be carried out under the same conditions as described in Step D3 of Method D.

Step E3

In this step, the compound of formula (VIII) is prepared by the deprotection of the compound of formula (XVIII) or (XIX) prepared as described in Step E1 or E2. The reaction may be carried out under the same conditions as described in Step D1 of Method D.

The compounds of formula (I), and the intermediates above-mentioned preparation methods can be isolated and purified by conventional procedures, such as distillation, recrystallization or chromatographic purification.

The optically active compounds of this invention can be prepared by several methods. For example, the optically active compounds of this invention may be obtained by chromatographic separation, enzymatic resolution or fractional crystallization from the final compounds.

Several compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, pharmaceutically acceptable esters of said compounds and pharmaceutically acceptable salts of said compounds, of said esters or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assay. Tritiated, i.e., $^3H$, and carbon-14, i.e., $^{14}C$, isotopes are particularly preferred for their ease of presentation and detectability. Further, substitution with heavier isotopes such as deuterium, i.e., $^2H$, can afford therapeutic advantage resulting from greater metabolic stability, for example increased in vivo half-life or reduced dosage requirement and, hence, may be preferred in some circumstances. Isotopically labeled compounds of formula (I) of this invention and prodrugs thereof can generally be prepared by carrying out the procedure disclosed in above-disclosed Schemes and/or Examples and Preparations below, by submitting a readily available isotopically labeled reagent for a non-isotopically labeled reagent.

The present invention includes salt forms of the compounds (I) as obtained.

Certain compounds of the present invention may be capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases which are used to prepare the pharmaceutically acceptable base addition salts of the acidic compounds of this invention of formula (I) are those which form non-toxic base addition salts, i.e., salts containing pharmaceutically acceptable cations, such as adenine, arginine, cytosine, lysine, benethamine (i.e., N-benzyl-2-phenyletylamine), benzathine (i.e., N,N-dibenzylethylenediamine), choline, diolamine (i.e., diethanolamine), ethylenediamine, glucosamine, glycine, guanidine, guanine, meglumine (i.e., N-methylglucamine), nicotinamide, olamine (i.e., ethanolamine), ornithine, procaine, proline, pyridoxine, serine, tyrosine, valine and tromethamine (i.e., tris or tris(hydroxymethyl)aminomethane). The base addition salts can be prepared by conventional procedures.

Insofar as the certain compounds of this invention are basic compounds, they are capable of forming a wide variety of different salts with various inorganic and organic acids.

The acids which are used to prepare the pharmaceutically acceptable acid addition salts of the basic compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate, adipate, aspartate camsylate, edisylate (i.e., 1,2-ethanedisulfonate), estolate (i.e., laurylsulfate), gluceptate (i.e., gluscoheptonate), gluconate, 3-hydroxy-2-naphthoate, xionofoate (i.e., 1-hydroxy-2-naphthoate), isethionate, (i.e., 2-hydroxyethanesulfonate), mucate (i.e., galactarate), 2-naphsylate (i.e., naphthalenesulphonate, stearate, cholate, glucuronate, glutamate, hippurate, lactobionate, lysinate, maleate, mandelate, napadisylate, nicatinate, polygalacturonate, salicylate, sulphosalicylate, tannate, tryptophanate, borate, carbonate, oleate, phthalate and pamoate (i.e., 1.1'-methylene-bis-(2-hydroxy-3-naphthoate). The acid addition salts can be prepared by conventional procedures.

For a review of on suitable salts see Berge et al., J. Pharm. Sci., 66, 1-19, 1977.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. For example, it is possible to make a bioprecursor of the compounds of formula (I) in which one or both of L and W include hydroxy groups by making an ester of the hydroxy group. When only one of L and W includes hydroxy group, only mono-ester is possible. When both L and W include hydroxy, mono- and di-esters (which can be the same or different) can be made. Typical esters are simple alkanoate esters, such as acetate, propionate, butyrate, etc. In addition, when L or W includes a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride).

When the compounds of the formula (I) of this invention may form solvates such as hydrates, such solvates are included within the scope of this invention.

Method for Assessing Biological Activities:

The 5-HT$_4$ receptor binding affinities of the compounds of this invention are determined by the following procedures.

Human 5-HT$_4$ Binding

Human 5-HT$_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1000 dilution) and homogenized using a hand held Polytron PT 1200 disrupter set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 μl of test compounds were incubated with 25 μl of [$^3$H]-GR113808 (Amersham, final 0.2 nM) and 150 μl of membrane homogenate and WGA-SPA beads (Amersham) suspension solutions (10 μg protein and 1 mg SPA beads/well) for 60 minutes at room temperature. Nonspecific binding was determined by 1 μM GR113808 (Tocris) at the final concentration. Incubation was terminated by centrifugation at 1000 rpm. Receptor-bound radioactivity was quantified by counting with MicroBeta plate counter (Wallac).

The results are shown in Table 1.

TABLE 1

| Compound | Binding on Human 5HT4 [Ki (nM)] |
|---|---|
| Example 1 | 10.9 |
| Compound A | >500 |

Compound A is the following compound which is disclosed in WO2003/57688, mentioned above.

In this test, the compound of the present invention exhibited excellent binding activity selective for Human 5HT4.

Agonist-Induced cAMP Elevation in Human 5-HT$_{4(d)}$ Transfected HEK293 Cells

Human 5-HT$_{4(d)}$ transfected HEK293 cells were established in-house. The cells were grown at 37° C. and 5% CO$_2$ in DMEM supplemented with 10% FCS, 20 mM HEPES (pH 7.4), 200 μg/ml hygromycin B (Gibco), 100 units/ml penicillin and 100 μg/ml streptomycin.

The cells were grown to 60-80% confluence. On the previous day before treatment with compounds dialyzed FCS (Gibco) was substituted for normal and the cells were incubated overnight.

Compounds were prepared in 96-well plates (12.5 μl/well). The cells were harvested with PBS/1 mM EDTA, centrifuged and washed with PBS. At the beginning of the assay, cell pellet was resuspended in DMEM supplemented with 20 mM HEPES, 10 μM pargyline (Sigma) and 1 mM 3-isobutyl-1-methylxanthine (Sigma) at the concentration of 1.6×10$^5$ cells/ml and left for 15 minutes at room temperature. The reaction was initiated by addition of the cells into plates (12.5 μl/well). After incubation for 15 minutes at room temperature, 1% Triton X-100 was added to stop the reaction (25 μl/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 μs, window time 400 μs).

Data was analyzed based on the ratio of fluorescence intensity of each well at 620 nm and 665 nm followed by cAMP quantification using cAMP standard curve.

Enhancement of cAMP production elicited by each compound was normalized to the amount of cAMP produced by 1000 nM serotonin (Sigma).

All compounds of Examples showed 5HT$_4$ receptor agonistic activity.

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disrupter set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM MgCl$_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 μl in 96-well plates. Twenty μl of test compounds were incubated with 20 μl of [$^3$H]-dofetilide (Amersham, final 5 nM and 160 μl of membrane homogenate (25 μg protein) for 60 minutes at room temperature. Nonspecific binding was determined by 10 μM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM MgCl$_2$, pH 7.4 at 4° C. The filters were dried, put into sample bags and filled with Betaplate Scint. Radioactivity bound to filter was counted with Wallac Betaplate counter.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.5 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM CaCl$_2$ and 0.5 mM MgCl$_2$ (pH 6.5). The basolateral buffer consisted of Hanks Balanced Salt Solution, 25 mM D-glucose monohydrate, 20 mM HEPES Biological Buffer, 1.25 mM CaCl$_2$ and 0.5 mM MgCl$_2$ (pH 7.4). At the end of the preincubation, the media was removed and test compound solution (10 μM) in buffer was added to the apical compartment. The inserts were moved to wells containing fresh basolateral buffer at 1 hr. Drug concentration in the buffer was measured by LC/MS analysis.

Flux rate (F, mass/time) was calculated from the slope of cumulative appearance of substrate on the receiver side and apparent permeability coefficient (P$_{app}$) was calculated from the following equation.

$$P_{app}(cm/sec)=(F*VD)/(SA*MD)$$

where SA is surface area for transport (0.3 cm$^2$), VD is the donor volume (0.3 ml), MD is the total amount of drug on the donor side at t=0. All data represent the mean of 2 inserts. Monolayer integrity was determined by Lucifer Yellow transport.

The results are shown in Table 2.

TABLE 2

| Compound | Caco2 Permeability [$P_{app}$ (×10$^{-6}$cm/sec)] |
|---|---|
| Example 1 | 5.3 |
| Compound A | 0.2 |

In this test, the compound of the present invention exhibited excellent caco2 permeability.

The compounds of formula (I) of this invention can be administered via either the oral, parenteral or topical routes to mammals. In general, these compounds are most desirably administered to humans in doses ranging from 0.3 mg to 750 mg per day, preferably from 0.3 mg to 500 mg per day, although variations will necessarily occur depending upon the weight and condition of the subject being treated, the disease state being treated and the particular route of administration chosen. However, for example, a dosage level that is in the range of from 0.004 mg to 7 mg per kg of body weight per day is most desirably employed for treatment of gastroesophageal reflux disease.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oralpharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230-400 mesh ASTM or Fuji Silysia Chromatorex® DU3050 (Amino Type, 30~50 µm). Low-resolution mass spectral data (EI) were obtained on a Integrity (Waters) mass spectrometer or a Automass 120 (JEOL) mass spectrometer. Low-resolution mass spectral data (ESI) were obtained on a ZMD2 (Waters) mass spectrometer or a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.). Chemical symbols have their usual meanings; b.p. (boiling point), m.p. (melting point), (liter(s)), mL (milliliter(s)), g (gram(s)), mg (milligram(s)), mol (moles), mmol (millimoles), eq. (equivalent(s)).

Example 1

5-CHLORO-N-({1-[(4-HYDROXYTETRAHY-DRO-2H-PYRAN-4-YL)METHYL]PIPERIDIN-4-YL}METHYL)-1-ISOPROPYL-6-METHYL-2-OXO-1,2-DIHYDROPYRIDINE-3-CARBOXAMIDE AND HYDROCHLORIDE THEREOF

1(1) Benzyl({1-[(4-hydroxytetrahydro-2H-pyran-4-yl)methyl]piperidin-4-yl}methyl)-carbamate

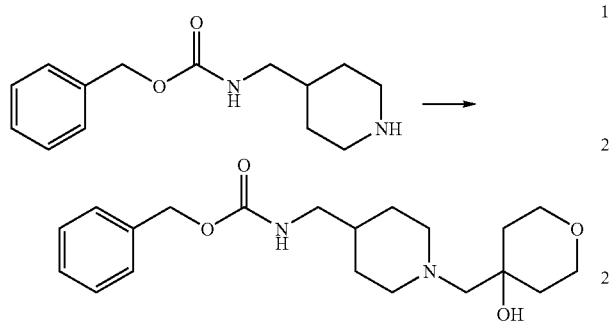

A mixture of benzyl(piperidin-4-ylmethyl)carbamate (7.77 g, 31.3 mmol, prepared according to Bose, D. Subhas et al., *Tetrahedron Lett.*, 1990, 31, 6903) and 1,6-dioxaspiro[2.5]octane (4.29 g, 37.6 mmol, prepared according to Satyamurthy, Nagichettiar et al., *Phosphorus Sulfur*, 1984, 19, 113) in methanol (93 mL) was stirred at room temperature for 20 h. Then, the mixture was refluxed for 8 h. After cooling to room temperature, the solvent was removed in vacuo. The residue was chromatographed on a column of silica gel eluting with dichloromethane/methanol (v/v=20/1) to give 5.60 g (49%) of the title compound as colorless oil.

$^1$H-NMR (CDCl$_3$) δ ppm: 7.40-7.30 (5H, m), 5.09 (2H, s), 4.85 (1H, br.), 3.85-3.72 (4H, m), 3.08 (2H, t, J=6.4 Hz), 2.88-2.83 (2H, m), 2.61 (1H, s), 2.36-2.30 (4H, m), 1.77-1.19 (9H, m).

1(2) 4-{[4-(Aminomethyl)piperidin-1-yl]methyl}tetrahydro-2H-pyran-4-ol

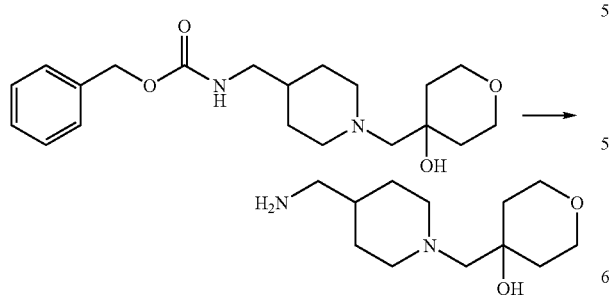

A mixture of benzyl({1-[(4-hydroxytetrahydro-2H-pyran-4-yl)methyl]piperidin-4-yl}methyl)carbamate as prepared in 1(1) (5.60 g, 15.5 mmol) and palladium on activated carbon (10 wt. %, 1.20 g) in methanol (250 mL) was hydrogenated at room temperature for 20 h. Then, the mixture was filtered through a pad of Celite, and the filtrate was concentrated in vacuo to give 3.30 g (94%) of the title compound as slightly yellow oil.

MS (ESI) m/z: 229 (M+H)$^+$.

$^1$H-NMR (CDCl$_3$) δ ppm: 3.70-3.81 (4H, m), 2.85-2.90 (2H, m), 2.57 (2H, d, J=5.7 Hz), 2.35 (2H, t, J=11.0 Hz), 2.32 (2H, s), 1.65-1.71 (2H, m), 1.44-1.63 (8H, m), 1.19-1.28 (2H, m).

1(3) tert-Butyl ({1-[(4-hydroxytetrahydro-2H-pyran-4-yl)methyl]piperidin-4-yl}methyl)carbamate

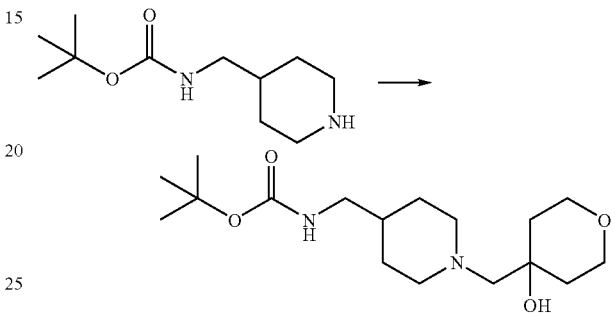

To a stirred solution of tert-butyl(piperidin-4-ylmethyl)carbamate (22.3 g, 104 mmol) in methanol (120 mL) was added 1,6-dioxaspiro[2.5]octane (14.2 g, 124 mmol, prepared according to Satyamurthy, Nagichettiar et al., *Phosphorus Sulfur*, 1984, 19, 113) at room temperature. Then, the mixture was heated at 60° C. for 4 h. The volatile components were removed by evaporation and the resulting viscous oil was precipitated with a mixture of hexane and diethyl ether. The precipitate was collected by filtration and recrystallized from a mixture of n-hexane and 2-propanol to give the title compound 14.2 g (42%) as a colorless powder.

MS (ESI) m/z: 329 (M+H)$^+$.

m.p.: 104° C.

$^1$H-NMR (CDCl$_3$) δ ppm: 3.85-3.70 (4H, m), 3.00 (2H, t, J=6.2 Hz), 2.88-2.83 (2H, m), 2.38-2.27 (4H, m), 1.69-1.51 (8H, m), 1.44 (9H, s), 1.31-1.23 (2H, m). A signal due to O$\underline{H}$ was not observed.

Anal. Calcd. for C$_{17}$H$_{32}$N$_2$O$_4$: C, 62.17; H, 9.82; N, 8.53. Found: C, 62.07; H, 9.92; N, 8.58.

1(4) 4-{[4-(Aminomethyl)piperidin-1-yl]methyl}tetrahydro-2H-pyran-4-ol

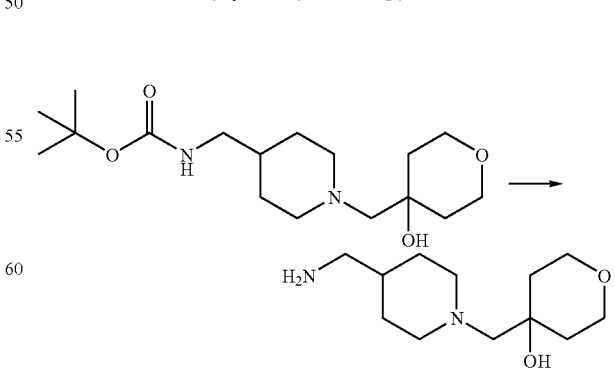

To a solution of tert-butyl ({1-[(4-hydroxytetrahydro-2H-pyran-4-yl)methyl]piperidin-4-yl}methyl)carbamate as prepared in 1(3) (50.28 g, 153 mmol) in methanol (100 mL) was added 4N hydrochloric acid dioxane solution (200 mL, 800 mmol) at room temperature. After 4 h, the volatile materials were removed by evaporation. The resulting amorphous was precipitated with diethyl ether/methanol (v/v=5/1). The precipitate was collected and added to the ice cooled 6N aqueous sodium hydroxide solution (200 mL) gradually. The mixture was extracted with dichloromethane/methanol (v/v=10/1, 500 mL×4). The combined organic layers were washed with brine, dried over magnesium sulfate and concentrated in vacuo to give 24.90 g (99%) of the title compound as a pale brown amorphous solid.

MS (ESI) m/z: 229 (M+H)$^+$.

$^1$H-NMR (CDCl$_3$) δ ppm: 3.70-3.81 (4H, m), 2.85-2.90 (2H, m), 2.57 (2H, d, J=5.7 Hz), 2.35 (2H, t, J=11.0 Hz), 2.32 (2H, s), 1.65-1.71 (2H, m), 1.44-1.63 (8H, m), 1.19-1.28 (2H, m).

1(5) Ethyl 1-isopropyl-6-methyl-2-oxo-1,2-dihydro-pyridine-3-carboxylate

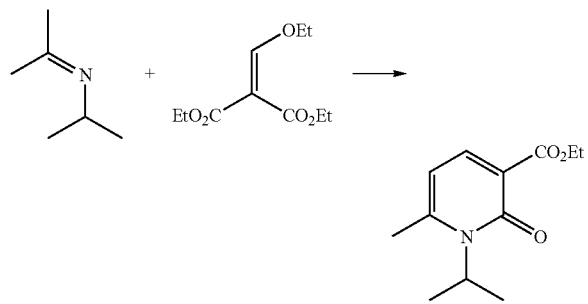

A mixture of isopropyl(1-methylethylidene)amine (7.94 g, 80.0 mmol, prepared according to Newcomb, Martin et al., *J. Amer. Chem. Soc.*, 1990, 112, 5186) and diethyl(ethoxymethylene)malonate (17.31 g, 80.0 mmol) in diphenyl ether (48 mL) was stirred in a sealed tube at 180-190° C. for 18 h. After cooling, the mixture was chromatographed on a column of silica gel eluting with n-hexane/ethyl acetate (v/v=1/1~1/2) to give 12.5 g (70%) of the title compound as brown oil.

MS (ESI) m/z: 224 (M+H)$^+$, 222 (M−H)$^−$.

$^1$H-NMR (CDCl$_3$) δ ppm: 7.93 (1H, d, J=7.4 Hz), 5.99 (1H, d, J=7.4 Hz), 4.48 (1H, br.), 4.33 (2 H, q, J=7.1 Hz), 2.41 (3H, s), 1.63 (6H, d, J=6.8 Hz), 1.34 (3H, t, J=7.1 Hz).

1(6) Ethyl 5-chloro-1-isopropyl-6-methyl-2-oxo-1,2-dihydropyridine-3-carboxylate

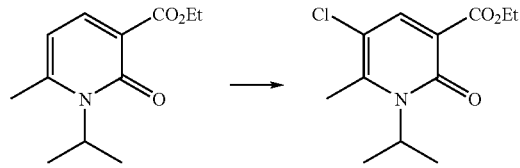

A mixture of ethyl 1-isopropyl-6-methyl-2-oxo-1,2-dihydropyridine-3-carboxylate as prepared in 1(5) (3.0 g, 13.44 mmol) and N-chlorosuccinimide (1.79 g, 13.44 mmol) in N,N-dimethylformamide (27 mL) was stirred at room temperature for 16 h, and the solvent was removed in vacuo. The residue was chromatographed on a column of silica gel eluting with n-hexane/ethyl acetate (v/v=2/1~1/1) to give 3.19 g (92%) of the title compound as brown oil.

MS (ESI) m/z: 258 (M+H)$^+$, 256 (M−H)$^−$.

$^1$H-NMR (CDCl$_3$) δ ppm: 8.02 (1H, s), 4.72 (1H, br.), 4.34 (2H, q, J=7.2 Hz), 2.56 (3H, s), 1.62 (6H, d, J=6.8 Hz), 1.36 (3H, t, J=7.2 Hz).

1(7) 5-Chloro-1-isopropyl-6-methyl-2-oxo-1,2-dihydropyridine-3-carboxylic acid

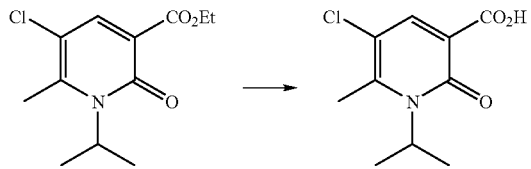

To a stirred solution of ethyl 5-chloro-1-isopropyl-6-methyl-2-oxo-1,2-dihydropyridine-3-carboxylate as prepared in 1(6) (203 mg, 0.79 mmol) in tetrahydrofuran (2 mL) and methanol (2 mL) was added 2N sodium hydroxide aqueous solution (2 mL) at room temperature, and the mixture was stirred at room temperature for 16 h. Then, the solvent was removed in vacuo. The residue was diluted with water (30 mL), acidified with 2N hydrochloric acid aqueous solution (pH~2) and extracted with dichloromethane (50 mL×3). The combined organic layers were dried over magnesium sulfate and concentrated in vacuo to give 171 mg (94%) of the title compound as a white solid.

MS (ESI) m/z: 230 (M+H)$^+$, 228 (M−H)$^−$.

$^1$H-NMR (CDCl$_3$) δ ppm: 14.16 (1H, s), 8.42 (1H, s), 4.74 (1H, br.), 2.67 (3H, s), 1.68 (6H, d, J=6.8 Hz).

1(8) 5-Chloro-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide and hydrochloride thereof

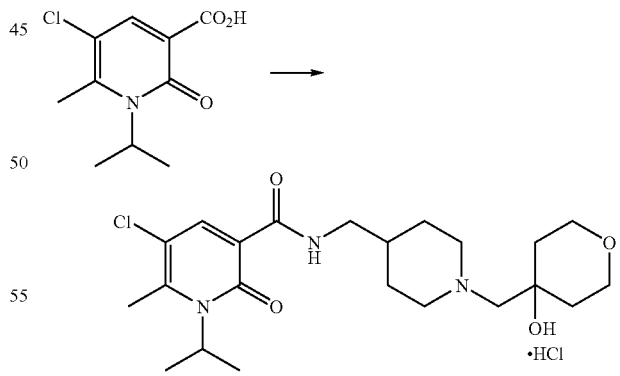

To a solution of 5-chloro-1-isopropyl-6-methyl-2-oxo-1,2-dihydropyridine-3-carboxylic acid as prepared in 1(7) (171 mg, 0.745 mmol) in dichloromethane (3 mL) were added oxalyl chloride (284 mg, 2.24 mmol) and a drop of N,N-dimethylformamide at room temperature, and the mixture was stirred at room temperature for 2 h. The solvent and excess amounts of oxalyl chloride were removed in vacuo. The residue was dissolved in dichloromethane (2 mL). To the resulting solution were added 4-{[4-(aminomethyl)piperidin-1-yl]methyl}tetrahydro-2H-pyran-4-ol as prepared in 1(2) and 1(4) (255 mg, 1.12 mmol), N,N-diisopropylethylamine (144 mg, 1.12 mmol) at room temperature for 18 h, and the mixture was stirred at room temperature for 18 h.

Then, the mixture was quenched with saturated sodium hydrogencarbonate aqueous solution (50 mL), and extracted with dichloromethane (50 mL×3). The combined organic layers were dried over magnesium sulfate and concentrated in vacuo. The residue was purified with plate TLC eluting with dichloromethane/methanol (v/v=20/1~15/1) to give the title compound as a salt free form.

This was treated with 10% hydrogen chloride in methanol, and the solvent was removed in vacuo The residue was crystallized in 2-propanol to give 187 mg (53%) of the title compound as a white solid.

MS (ESI) m/z: 440 (M+H)$^+$.

m.p.: 283° C. (decomposition).

IR (KBr) ν: 3321, 2858, 2529, 1674, 1618, 1533, 1439, 1350, 1304, 1254, 1169, 1142, 1105, 1022, 991, 945, 899, 856, 799, 698, 606, 548 cm$^{-1}$.

$^1$H-NMR (DMSO-$d_6$) δ ppm: 9.67 (1H, br.), 8.15 (1H, s), 4.77 (1H, br.), 3.60-3.55 (5H, m), 3.33 (3H, s), 3.30-2.93 (9H, m), 1.74-1.52 (13H, m). A signal due to O$\underline{H}$ was not observed.

Anal. Calcd. for $C_{22}H_{34}N_3O_4Cl \cdot HCl \cdot 0.1H_2O$: C, 55.25; H, 7.42; N, 8.79. Found: C, 54.96; H, 7.49; N, 8.79.

Example 2

5-CHLORO-6-ETHYL-N-({1-[(4-HYDROXYTETRAHYDRO-2H-PYRAN-4-YL)METHYL]PIPERIDIN-4-YL}METHYL)-1-ISOPROPYL-2-OXO-1,2-DIHYDROPYRIDINE-3—CARBOXAMIDE AND ETHANEDIOATE THEREOF

2(1) Ethyl 6-ethyl-1-isopropyl-2-oxo-1,2-dihydropyridine-3-carboxylate

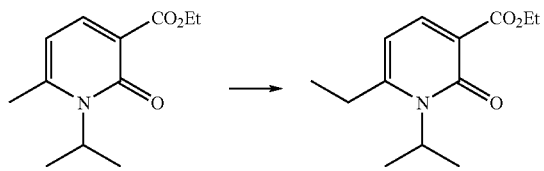

To a stirred solution of ethyl 1-isopropyl-6-methyl-2-oxo-1,2-dihydropyridine-3-carboxylate as prepared in Example 1(5) (515 mg, 2.0 mmol) in tetrahydrofuran (3 mL) was added a solution of lithium diisopropylamide (2.0M, 1.0 mL, 1.0 mmol) dropwise at −30° C. over 40 min. After addition, the mixture was stirred at 0° C. for 3 h. Then, methyl iodide (426 mg, 3.0 mmol) was added at 0° C., and the mixture was stirred at room temperature for 16 h. The mixture was quenched with water (5.0 mL), and extracted with dichloromethane (30 mL×3). The combined organic layers were dried over magnesium sulfate and concentrated in vacuo. The residue was purified with plate TLC eluting with n-hexane/ethyl acetate (v/v=2/1) to give 110 mg (23%) of the title compound as yellow oil.

$^1$H-NMR (CDCl$_3$) δ ppm: 7.95 (1H, d, J=7.6 Hz), 6.00 (1H, d, J=7.4 Hz), 4.45 (1H, br.), 4.32 (2H, q, J=7.1 Hz), 2.67 (2H, q, J=7.4 Hz), 1.64 (6H, d, J=6.8 Hz), 1.33 (3H, t, J=7.1 Hz), 1.26 (3H, t, J=7.4 Hz).

2(2) Ethyl 5-chloro-6-ethyl-1-isopropyl-2-oxo-1,2-dihydropyridine-3-carboxylate

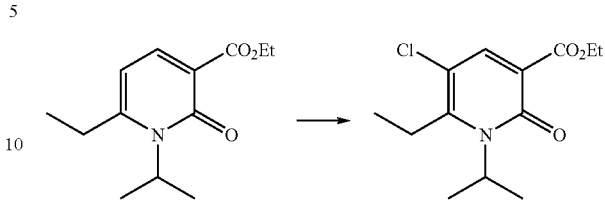

The title compound was prepared according to the procedure of Example 1(6), but using ethyl 6-ethyl-1-isopropyl-2-oxo-1,2-dihydropyridine-3-carboxylate as prepared in 2(1) instead of ethyl 1-isopropyl-6-methyl-2-oxo-1,2-dihydropyridine-3-carboxylate.

$^1$H-NMR (CDCl$_3$) δ ppm: 7.97 (1H, s), 4.44 (1H, br.), 4.31 (2H, q, J=7.1 Hz), 2.88 (2H, q, J=7.4 Hz), 1.63 (6H, d, J=6.6 Hz), 1.32 (3H, t, J=71 Hz), 1.22 (3H, t, J=7.4 Hz).

2(3) 5-Chloro-6-ethyl-1-isopropyl-2-oxo-1,2-dihydropyridine-3-carboxylic acid

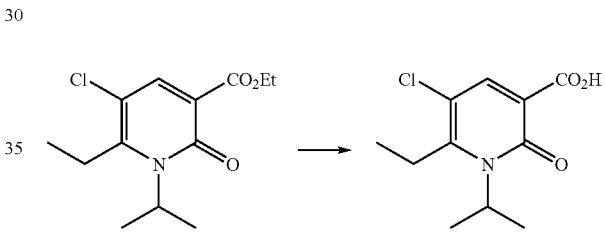

The title compound was prepared according to the procedure of Example 1(7), but using ethyl 5-chloro-6-ethyl-1-isopropyl-2-oxo-1,2-dihydropyridine-3-carboxylate as prepared in 2(2) instead of ethyl 5-chloro-1-isopropyl-6-methyl-2-oxo-1,2-dihydropyridine-3-carboxylate.

MS (ESI) m/z: 244 (M+H)$^+$, 242 (M−H)$^-$.

$^1$H-NMR (CDCl$_3$) δ ppm: 14.52 (1H, br.), 8.37 (1H, s), 4.64 (1H, br.), 3.00 (2H, q, J=7.5 Hz), 1.68 (6H, d, J=6.8 Hz), 1.28 (3H, 1, J=7.5 Hz).

2(4) 5-Chloro-6-ethyl-N-({1-[(4-hydroxytetrahydro-2H-pyran-4-yl)methyl]piperidin-4-yl}methyl)-1-isopropyl-2-oxo-1,2-dihydropyridine-3-carboxamide and ethanedioate thereof

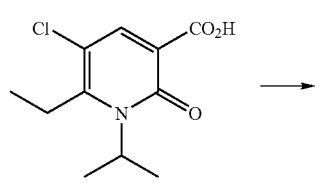

29
-continued

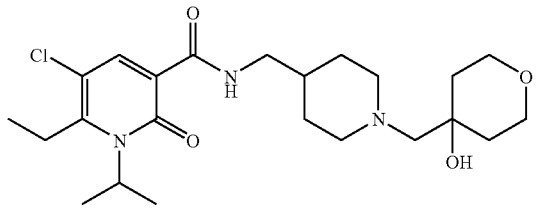

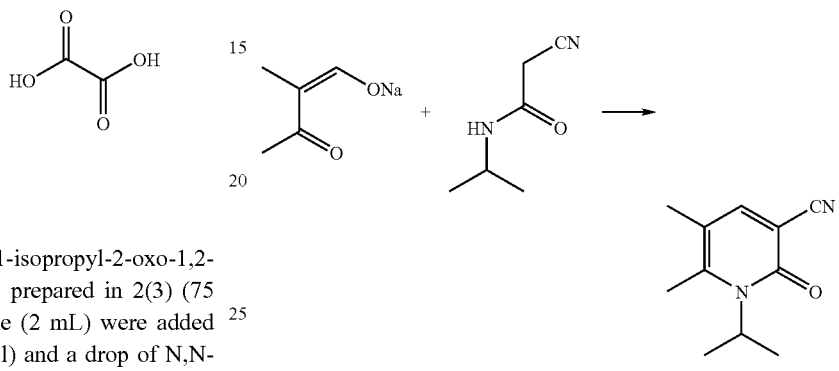

To a solution of 5-chloro-6-ethyl-1-isopropyl-2-oxo-1,2-dihydropyridine-3-carboxylic acid as prepared in 2(3) (75 mg, 0.308 mmol) in dichloromethane (2 mL) were added oxalyl chloride (117 mg, 0.923 mmol) and a drop of N,N-dimethylformamide at room temperature, and the mixture was stirred at room temperature for 2 h. The solvent and excess amounts of oxalyl chloride were removed in vacuo. The residue was dissolved in dichloromethane (2 mL). To the resulting solution were added 4-{[4-(aminomethyl)piperidin-1-yl]methyl}tetrahydro-2H-pyran-4-ol as prepared in Example 1(2) and 1(4) (105 mg, 0.462 mmol), N,N-diisopropylethylamine (60 mg, 0.462 mmol) at room temperature, and the mixture was stirred at room temperature for 18 h. Then, the mixture was quenched with saturated sodium hydrogencarbonate aqueous solution (30 mL), and extracted with dichloromethane (30 mL×3). The combined organic layers were dried over magnesium sulfate and concentrated in vacuo. The residue was purified with plate TLC eluting with dichloromethane/methanol/25% ammonium hydroxide (v/v/v=10/1/0.2) to give 122 mg (87%) of the title compound as a salt free form.

This was treated with oxalic acid in 2-propanol, and recrystallized to give 87 mg (52%) of the title compound as a white solid.

MS (ESI) m/z: 454 (M+H)$^+$, 452 (M−H)$^−$.

m.p.: 123° C. (decomposition).

IR (KBr) ν: 3254, 2939, 2860, 2415, 1767, 1668, 1616, 526, 1454, 1356, 1167, 1097, 1061, 1020, 982, 949, 845, 800, 718, 673, 613 cm$^{-1}$.

$^1$H-NMR (DMSO-d$_6$) δ ppm: 9.67 (1H, br.), 8.16 (1H, s), 4.68 (1H, br.), 3.60-3.58 (4H, m), 3.41-3.37 (2H, m), 3.24-3.21 (2H, m), 2.99-2.77 (6H, m), 1.73-1.45 (9H, m), 1.66 (6H, d, J=6.6 Hz), 1.16 (3H, t, J=7.1 Hz). A signal due to O$\underline{H}$ was not observed.

Anal. Calcd. for C$_{23}$H$_{36}$N$_3$O$_4$Cl.C$_2$H$_2$O$_4$.1.0C$_3$H$_8$O (2-propanol)+1.0H$_2$O: C, 54.05; H, 7.78; N, 6.75. Found: C, 54.11; H, 7.66; N, 6.80.

30

Example 3

N-({1-[(4-HYDROXYTETRAHYDRO-2H-PYRAN-4-YL)METHYL]PIPERIDIN-4-YL}METHYL)-1-ISOPROPYL-5,6-DIMETHYL-2-OXO-1,2-DIHYDROPYRIDINE-3-CARBOXAMIDE AND ETHANEDIOATE THEREOF

3(1) 1-Isopropyl-5,6-dimethyl-2-oxo-1,2-dihydropyridine-3-carbonitrile

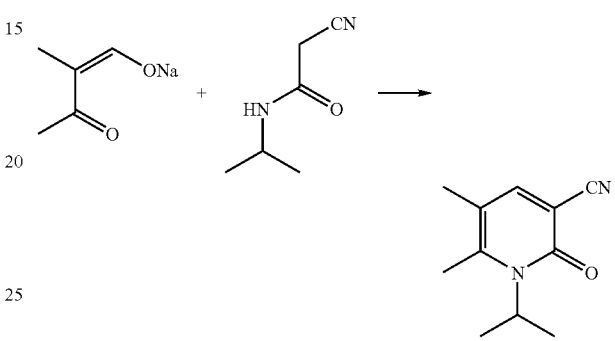

To a stirred solution of 2-methyl-3-oxobutanal sodium salt (2.73 g, 22.4 mmol, prepared according to Paine, John B et al., *J. Heterocycl. Chem.*, 1987, 24, 351), 2-cyano-N-isopropylacetamide (2.17 g, 17.2 mmol, prepared according to Wuerthner, Frank et al., *J. Amer. Chem. Soc.*, 2002, 32, 9431) in N,N-dimethylformamide (17.2 mL) were added piperidine (292 mg, 3.43 mmol) and acetic acid (1.34 g, 22.4 mmol) successively at room temperature, and the mixture was stirred at 135° C. for 7 h. After cooling, the mixture was quenched with water (100 mL), extracted with dichloromethane (50 mL×4). The combined organic layers were dried over magnesium sulfate and concentrated in vacuo. The residue was chromatographed on a column of silica gel eluting with n-hexane/ethyl acetate (v/v=2/1~1/1) to give 840 mg (26%) of the title compound as an orange colored solid.

MS (ES) m/z: 191 (M+)$^+$, 189 (M−H)$^−$.

$^1$H-NMR (CDCl$_3$) δ ppm: 7.48 (1H, s), 4.71 (1H, br.), 2.36 (3H, s), 2.06 (3H, s), 1.54 (6H, d, J=6.8 Hz).

3(2) 1-Isopropyl-5,6-dimethyl-2-oxo-1,2-dihydropyridine-3-carboxylic acid

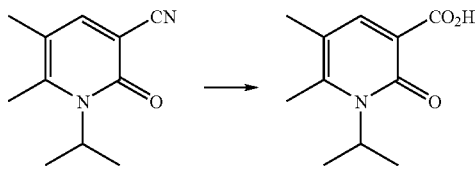

A mixture or 1-isopropyl-5,6-dimethyl-2-oxo-1,2-dihydropyridine-3-carbonitrile as prepared in 3(1) (840 mg, 4.42 mmol), potassium hydroxide (1.84 g, 32.7 mmol), ethanol (12 μL) and water (3 mL) was refluxed for 16 h. After cooling, the mixture was concentrated in vacuo. The aqueous residue was diluted with water (80 mL), washed with ethyl acetate (80 mL), and acidified with 2N hydrochloric acid aqueous solu-

3(3) N-({1-[(4-Hydroxytetrahydro-2H-pyran-4-yl)methyl]piperidin-4-yl}methyl)-1-isopropyl-5,6-dimethyl-2-oxo-1,2-dihydropyridine-3-carboxamide and ethanedioate thereof

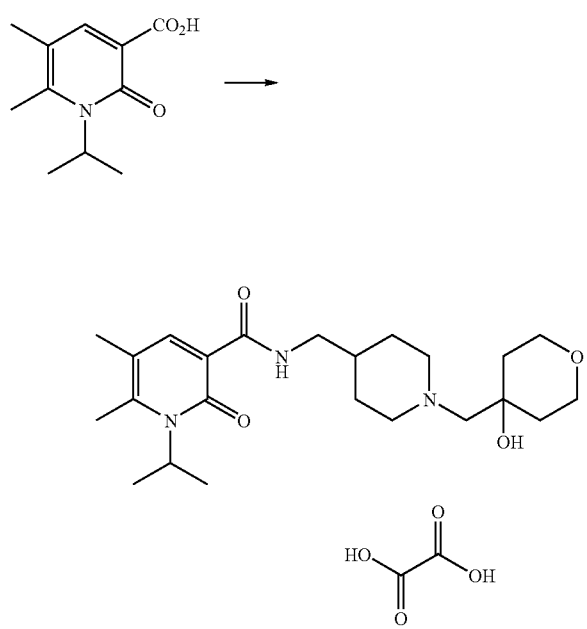

The title compound was prepared according to the procedure of Example 2(4), but using 1-isopropyl-5,6-dimethyl-2-oxo-1,2-dihydropyridine-3-carboxylic acid as prepared in 3(2) instead of 5-chloro-6-ethyl-1-isopropyl-2-oxo-1,2-dihydropyridine-3-carboxylic acid.

MS (ESI) m/z: 420 (M+H)$^+$, 418 (M−H)$^-$.

m.p.: 178° C. (decomposition).

IR (KBr) v: 3209, 2922, 2872, 2536, 1665, 1609, 1537, 1450, 1362, 1306, 1221, 1186, 1099, 1018, 951, 851, 800, 719, 617 cm$^{-1}$.

$^1$H-NMR (DMSO-d$_6$) δ ppm: 9.92 (1H, br.), 8.08 (1H, s), 4.32 (1H, br.), 3.60-3.58 (4H, m), 3.41-3.37 (2H, m), 3.23-3.19 (2H, m), 2.94-2.84 (4H, m), 2.40 (3H, s), 2.12 (3H, s), 1.74-1.45 (9H, m), 1.62 (6H, d, J=6.8 Hz). A signal due to OH was not observed.

Anal. Calcd. for C$_{23}$H$_{37}$N$_3$O$_4$·C$_2$H$_2$O$_4$·1.1H$_2$O: C, 56.72; H, 7.84; N, 7.94. Found: C, 56.43; H, 8.09; N, 7.67.

Example 4

5-BROMO-N-({1-[(4-HYDROXYTETRAHYDRO-2H-PYRAN-4-YL)METHYL]PIPERIDIN-4-YL}METHYL)-1-ISOPROPYL-6-METHYL-2-OXO-1,2-DIHYDROPYRIDINE-3-CARBOXAMIDE AND ETHANEDIOATE THEREOF

4(1) Ethyl 5-bromo-1-isopropyl-6-methyl-2-oxo-1,2-dihydropyridine-3-carboxylate

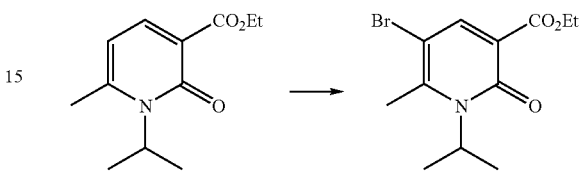

A mixture of ethyl 1-isopropyl-6-methyl-2-oxo-1,2-dihydropyridine-3-carboxylate as prepared in Example 1(5) (1.12 g, 5.00 mmol) and N-bromosuccinimide (890 mg, 5.00 mmol) in N,N-dimethylformamide (10 mL) was stirred at room temperature for 16 h, and then the solvent was removed in vacuo. The residue was chromatographed on a column of silica gel eluting with n-hexane/ethyl acetate (v/v=2/1~1/1) to give 1.34 g (91%) of the title compound as a yellow solid.

MS (ESI) m/z: 302 (M+H)$^+$, 300 (M−H)$^-$.

$^1$H-NMR (CDCl$_3$) δ ppm: 8.14 (1H, s), 4.72 (1H, br.), 4.35 (2-H, q, J=7.2 Hz), 2.62 (3H, s), 1.63 (6H, d, J=6.8 Hz), 1.37 (3H, t, J=7.2 Hz).

4(2) 5-Bromo-1-isopropyl-6-methyl-2-oxo-1,2-dihydropyridine-3-carboxylic acid

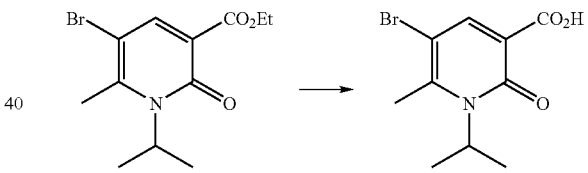

The title compound was prepared according to the procedure of Example 1(7), but using ethyl 5-bromo-1-isopropyl-6-methyl-2-oxo-1,2-dihydropyridine-3-carboxylate as prepared in 4(1) instead of ethyl 5-chloro-1-isopropyl-6-methyl-2-oxo-1,2-dihydropyridine-3-carboxylate.

MS (ESI) m/z: 274 (M+H)$^+$, 272 (M−H)$^-$.

$^1$H-NMR (CDCl$_3$) δ ppm: 14.43 (1H, s), 8.54 (1H, s), 4.77 (1H, br.), 2.72 (3H, s), 1.67 (6H, d, J=6.9 Hz).

4(3) 5-Bromo-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide and ethanedioate thereof

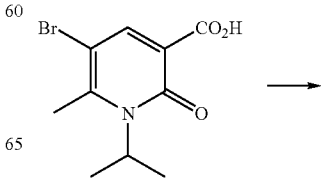

-continued

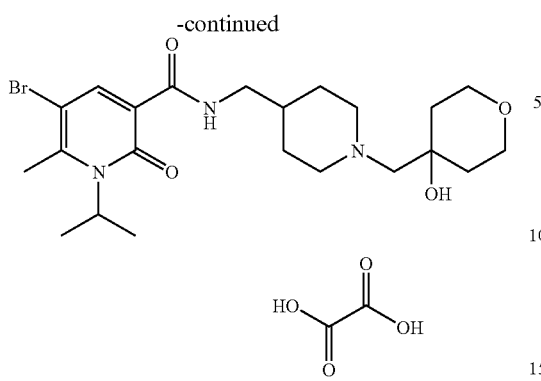

The title compound was prepared according to the procedure of Example 2(4), but using 5-bromo-1-isopropyl-6-methyl-2-oxo-1,2-dihydropyridine-3-carboxylic acid as prepared in 4(2) instead of 5-chloro-6-ethyl-1-isopropyl-2-oxo-1,2-dihydropyridine-3-carboxylic acid.

MS (ESI) m/z: 484 (M+H)$^+$, 482 (M–H)$^−$.

m.p.: 205° C. (decomposition).

IR (KBr) ν: 3271, 2936, 2864, 2353, 1767, 1614, 1529, 1454, 1344, 1248, 1204, 1167, 1099, 1022, 982, 949, 847, 800, 689, 613 cm$^{−1}$.

$^1$H-NMR (DMSO-d$_6$) δ ppm: 9.68 (1H, br.), 8.27 (1H, s), 4.78 (1H, br.), 3.65-3.57 (4H, m), 3.46-3.37 (2H, m), 3.27-3.21 (2H, m), 3.00-2.83 (4H, m), 2.67 (3H, s), 1.75-1.48 (9H, m), 1.65 (6H, d, J=3.3 Hz). A signal due to O$\underline{H}$ was not observed.

Anal. Calcd. for C$_{22}$H$_{34}$N$_3$O$_4$Br.C$_2$H$_2$O$_4$.0.5H$_2$O: C, 49.40; H, 6.39; N, 7.20. Found: C, 49.06; H, 6.33; N, 6.91.

Example 5

5-FLUORO-N-({1-[(4-HYDROXYTETRAHYDRO-2H-PYRAN-4-YL)METHYL]PIPERIDIN-4-YL}METHYL)-1-ISOPROPYL-6-METHYL-2-OXO-1,2-DIHYDROPYRIDINE-3-CARBOXAMIDE

5(1) Ethyl 5-fluoro-1-isopropyl-6-methyl-2-oxo-1,2-dihydropyridine-3-carboxylate

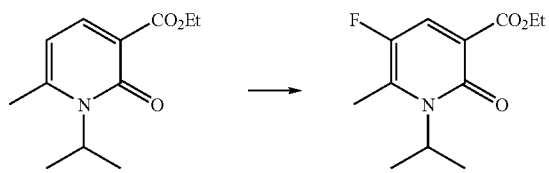

A mixture of ethyl 1-isopropyl-6-methyl-2-oxo-1,2-dihydropyridine-3-carboxylate as prepared in Example 1(5) (2.23 g, 10.0 mmol) and 1-(chloromethyl)-4-fluoro-1,4-diazoniabicyclo[2.2.2]octane bis(tetrafluoroborate) (3.76 g, 10.6 mmol) in acetonitrile (80 mL) was stirred at room temperature for 16 h. The mixture was quenched with water (300 mL), and extracted with ethyl acetate (100 mL×4). The combined organic layers were washed with water (100 mL×6), brine (100 mL), dried over magnesium sulfate and concentrated in vacuo. The residue was chromatographed on a column of silica gel eluting with n-hexane/ethyl acetate (v/v=2/1~1/1) to give 572 mg (24%) of the title compound as a yellow solid.

MS (ESI) m/z: 242 (M+H)$^+$.

$^1$H-NMR (CDCl$_3$) δ ppm: 7.91 (1H, d, J=8.8 Hz), 4.50 (1H, br.), 4.29 (2H, q, J=7.2 Hz), 2.36 (3H, d, J=3.1 Hz), 1.58 (6H, d, J=6.8 Hz), 1.31 (3H, t, J=7.0 Hz).

5(2) 5-Fluoro-1-isopropyl-6-methyl-2-oxo-1,2-dihydropyridine-3-carboxylic acid

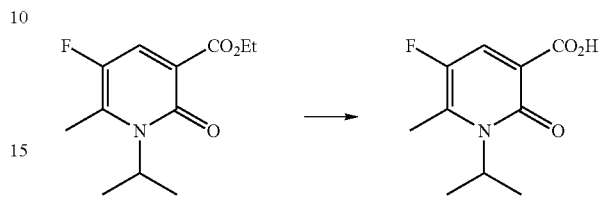

The title compound was prepared according to the procedure of Example 1(7), but using ethyl 5-fluoro-1-isopropyl-6-methyl-2-oxo-1,2-dihydropyridine-3-carboxylate as prepared in 5(1) instead of ethyl 5-chloro-1-isopropyl-6-methyl-2-oxo-1,2-dihydropyridine-3-carboxylate.

MS (ESI) m/z: 214 (M+H)$^+$, 212 (M–H)$^−$.

$^1$H-NMR (CDCl$_3$) δ ppm: 14.77 (1H, s), 8.30 (1H, d, J=8.1 Hz), 4.65 (1H, br.), 2.52 (3H, d, J=3.1 Hz), 1.68 (6H, d, J=6.9 Hz).

5(3) 5-Fluoro-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide

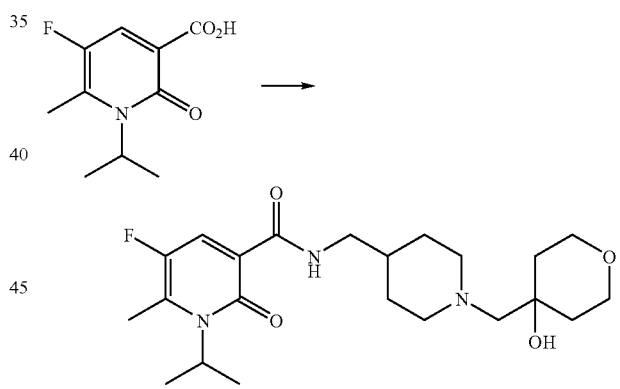

To solution of 5-fluoro-1-isopropyl-6-methyl-2-oxo-1,2-dihydropyridine-3-carboxylic acid as prepared in 5(2) (213 mg, 1.0 mmol) in dichloromethane (10 mL) were added oxalyl chloride (381 mg, 3.0 mmol) and a drop of N,N-dimethylformamide at room temperature. The mixture was stirred at room temperature for 2 h. The solvent and excess amounts of oxalyl chloride were removed in vacuo. The residue was dissolved in dichloromethane (7 mL). To the resulting solution were added 4-{[4-(aminomethyl)piperidin-1-yl]methyl}tetrahydro-2H-pyran-4-ol as prepared in Example 1(2) and 1(4) (342 mg, 1:50 mmol), N,N-diisopropylethylamine (194 mg, 1.50 mmol) at room temperature and the mixture was stirred at room temperature for 18 h. Then, the mixture was quenched with saturated sodium hydrogencarbonate aqueous solution (30 mL), and extracted with dichloromethane (50 mL×4). The combined organic layers were dried over magnesium sulfate and concentrated in vacuo. The residue was purified with plate TLC eluting with dichloromethane/methanol (20/1) to give 275 mg (65%) of the title compound as a white solid.

MS (ESI) m/z: 424 (M+H)+, 422 (M−H)−.

m.p.: 133° C. (decomposition).

IR (KBr) ν: 2870, 1676, 1624, 1551, 1448, 1371, 1348, 1225, 1200, 1155, 1107, 1065, 1011, 935, 889, 841, 797, 710 cm−1.

1H-NMR (CDCl3) δ ppm: 9.91 (1H, br.), 8.32 (1H, d, J=9.2 Hz), 4.55 (1H, br.), 3.81-3.68 (4H, m), 3.29 (2H, t, J=6.2 Hz), 2.86-2.83 (2H, m), 2.41-2.32 (4H, m), 2.28 (3H, s), 1.72-1.23 (9H, m), 1.62 (6H, d, J=6.8 Hz). A signal due to OH was not observed.

Anal. Calcd. for $C_{22}H_{34}N_3O_4F \cdot 0.03H_2O$: C, 62.31; H, 8.10; N, 9.91. Found: C, 61.91; H, 8.13; N, 9.98.

Example 6

5-CHLORO-N-{[1-(CYCLOHEXYLMETHYL)PIPERIDIN-4-YL]METHYL}-1-ISOPROPYL-6-METHYL-2-OXO-1,2-DIHYDROPYRIDINE-3-CARBOXAMIDE

6(1) tert-Butyl 4-({[(5-chloro-1-isopropyl-6-methyl-2-oxo-1,2-dihydropyridin-3-yl)carbonyl]amino}methyl)piperidine-1-carboxylate

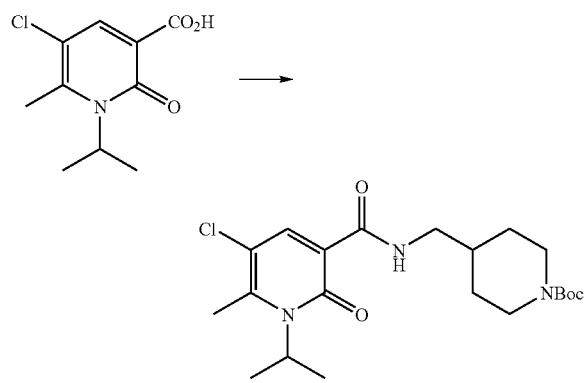

To a solution of 5-chloro-1-isopropyl-6-methyl-2-oxo-1,2-dihydropyridine-3-carboxylic acid as prepared in Example 1(7) (2.66 g, 11.6 mmol) in dichloromethane (30 mL) were added oxalyl chloride (4.41 g, 34.8 mmol) and a drop of N,N-dimethylformamide at room temperature, and the mixture was stirred at room temperature for 2 h. The solvent and excess amounts of oxalyl chloride were removed in vacuo. The residue was dissolved in dichloromethane (80 mL). To the resulting solution were added tert-butyl 4-(aminomethyl)piperidine-1-carboxylate (3.72 g, 17.4 mmol, prepared according to Carceller, Elena et al., J. Med. Chem., 1996, 39, 487), N,N-diisopropylethylamine (2.25 g, 17.4 mmol) at room temperature, and the mixture was stirred at room temperature for 18 h. Then, the mixture was quenched with saturated sodium hydrogencarbonate aqueous solution (100 mL), and extracted with dichloromethane (100 mL×4). The combined organic layers were dried over magnesium sulfate and concentrated in vacuo. The residue was chromatographed on a column of silica gel eluting with n-hexane/ethyl acetate (v/v=1/1) to give 5.27 g (99%) of the title compound as a white solid.

MS (ESI) m/z: 426 (M+H)+, 424 (M−H)−.

1H-NMR (CDCl3) δ ppm: 9.81 (1H, br.), 8.41 (1H, s), 4.73 (1H, br.), 4.13-4.06 (2H, m), 3.33-3.29 (2H, m), 2.72-2.64 (2H, m), 2.59 (3H, s), 1.75-1.71 (3H, m), 1.63 (6H, d, J=6.8 Hz), 1.44 (9H, s), 1.25-1.11 (2H, m).

6(2) 5-Chloro-1-isopropyl-6-methyl-2-oxo-N-(piperidin-4-ylmethyl)-1,2-dihydropyridine-3-carboxamide

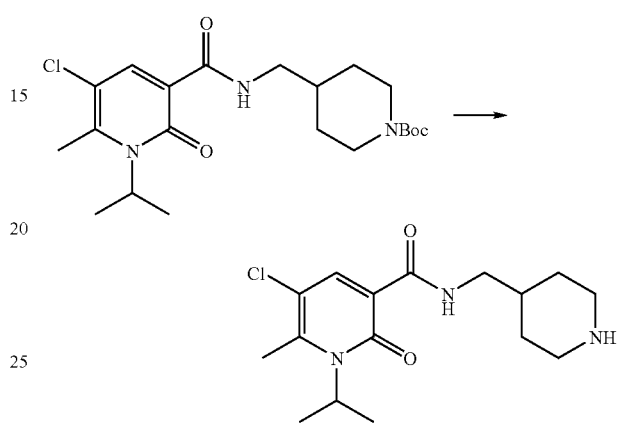

A mixture or tert-butyl 4-({[(5-chloro-1-isopropyl-6-methyl-2-oxo-1,2-dihydropyridin-3-yl)carbonyl]amino}methyl)piperidine-1-carboxylate as prepared in 6(1) (4.77 g, 11.2 mmol) in 10% hydrochloric acid methanol solution (30 mL) was stirred at room temperature for 18 h. The mixture was concentrated in vacuo. The residue was dissolved in methanol (15 mL) and tetrahydrofuran (15 mL). To the resulting solution was added potassium carbonate (3.0 g, 21.7 mmol) at room temperature, and the mixture was stirred at room temperature for 18 h. Then, the mixture was filtered through a pad of Celite, washed with methanol/tetrahydrofuran (v/v=1/1, 200 mL). The filtrate was concentrated in vacuo. The residue was chromatographed on a column of silica gel eluting with dichloromethane/methanol/25% ammonium hydroxide (v/v/v=10/1/0.2) to give 3.43 g (94%) of the title compound as a white solid.

MS (ESI) m/z: 326 (M+H)+, 324 (M−H)−.

1H-NMR (CDCl3) δ ppm: 9.98 (1H, br.), 8.41 (1H, s), 4.67 (1H, br.), 3.30 (2H, t, J=6.0 Hz), 3.10-3.06 (2H, m), 2.62-2.54 (5H, m), 1.77-1.12 (5H, m), 1.62 (6H, d, J=6.8 Hz). A signal due to NH was not observed.

6(3) 5-Chloro-N-{[1-(cyclohexylmethyl)piperidin-4-yl]methyl}-1-isopropyl-6-methyl-2-oxo-1,2-dihydropyridine-3-carboxamide

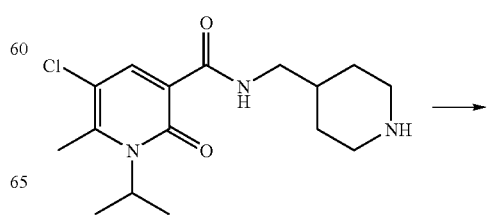

-continued

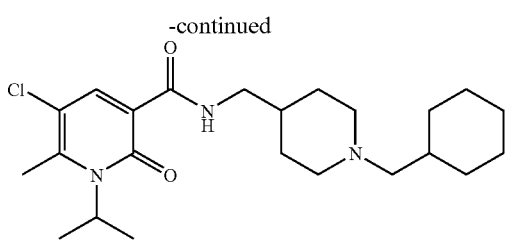

To a stirred solution of 5-chloro-1-isopropyl-6-methyl-2-oxo-N-(piperidin-4-ylmethyl)-1,2-dihydropyridine-3-carboxamide as prepared in 6(2) (228 mg, 0.70 mmol), cyclohexanecarboxaldehyde (94 mg, 0.84 mmol) in dichloromethane (11 mL) was added sodium triacetoxyborohydride (312 mg, 1.40 mmol) at room temperature, and the mixture was stirred at room temperature for 4 h. The mixture was quenched with saturated sodium hydrogencarbonate aqueous solution (80 mL), extracted with dichloromethane (50 mL×4). The combined organic layers were dried over magnesium sulfate and concentrated in vacuo. The residue was chromatographed on a column of silica gel eluting with dichloromethane/methanol (v/v=20/1) to give 213 mg (72%) of the title compound as a white solid.

MS (ESI) m/z: 422 (M+H)$^+$, 420 (M−H)$^-$.

m.p.: 168° C. (decomposition).

IR (KBr) ν: 3215, 2922, 2847, 1672, 1618, 1535, 1443, 1348, 1298, 1263, 1151, 1136, 1105, 1053, 1036, 988, 972, 945, 799, 694, 606, 536 cm$^{-1}$.

$^1$H-NMR (CDCl$_3$) δ ppm: 9.77 (1H, br.), 8.41 (1H, s), 4.72 (1H, br.), 3.81 (2H, t, J=6.3 Hz), 2.89-2.85 (2H, m), 2.58 (3H, s), 2.11-2.08 (2H, m), 1.91-1.11 (16H, m), 1.63 (6H, d, J=6.9 Hz), 0.91-0.79 (2H, m).

Anal. Calcd. for C$_{23}$H$_{36}$N$_3$O$_2$Cl: C, 65.46; H, 8.60; N, 9.96. Found: C, 65.10; H, 8.67; N, 9.79.

Example 7

5-CHLORO-N-({1-[(1-HYDROXYCYCLO-HEXYL)METHYL]PIPERIDIN-4-YL}METHYL)-1-ISOPROPYL-6-METHYL-2-OXO-1,2-DIHYDROPYRIDINE-3-CARBOXAMIDE

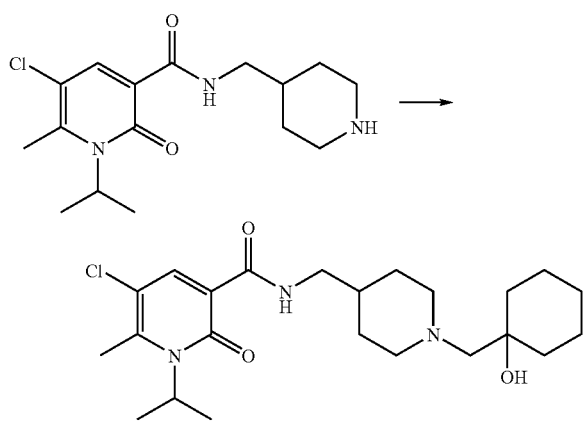

A mixture of 5-chloro-1-isopropyl-6-methyl-2-oxo-N-(piperidin-4-ylmethyl)-1,2-dihydropyridine-3-carboxamide as prepared in Example 6(2) (484 mg, 1.49 mmol) and 1-oxaspiro[2.5]octane (200 mg, 1.78 mmol, prepared according to Blake, Alexander J et al., *J. Chem. Soc. Dalton Trans.*, 1998, 14, 2335) in methanol (5 mL) was stirred at 50° C. for 16 h. Then, the solvent was removed in vacuo. The residue was chromatographed on a column of silica gel eluting with dichloromethane/methanol (v/v=20/1) to give 751 mg (99%) of the title compound as a white solid.

MS (ESI) m/z: 438 (M+H)$^+$, 436 (M−H)$^-$.

m.p.: 187° C. (decomposition).

IR (KBr) ν: 3215, 2922, 2853, 2758, 1672, 1620, 1537, 1439, 1350, 1300, 1275, 1169, 1140, 1115, 1082, 1053, 1036, 972, 945, 878, 799, 702 cm$^{-1}$.

$^1$H-NMR (CDCl$_3$) δ ppm: 9.78 (1H, br.), 8.41 (1H, s), 4.70 (1H, br.), 3.30 (2H, t, J=6.2 Hz), 2.89-2.85 (2H; m), 2.58 (3H, s), 2.34-2.28 (4H, m), 1.72-1.22 (15H, m), 1.62 (6H, d, J=6.8 Hz). A signal due to OH was not observed Anal. Calcd. for C$_{23}$H$_{36}$N$_3$O$_3$Cl.0.3H$_2$O: C, 62.30; H, 8.32; N, 9.48. Found: C, 62.39;

H, 8.27; N, 9.35.

Example 8

5-CHLORO-N-({1-[(CIS-1-HYDROXY-4-METH-OXYCYCLOHEXYL)METHYL]PIPERIDIN-4-YL}METHYL)-1-ISOPROPYL-6-METHYL-2-OXO-1,2-DIHYDROPYRIDINE-3-CARBOXAMIDE

8(1) 6-Methoxy-1-oxaspiro[2,5]octane

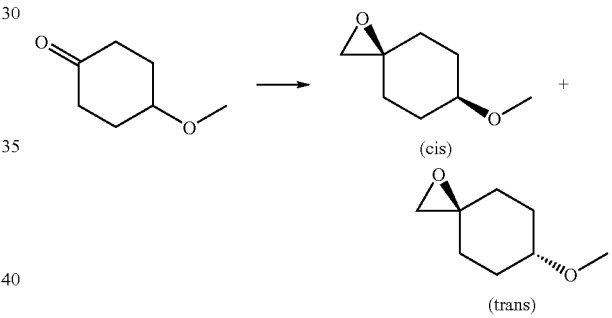

To a stirred suspension of sodium hydride (60% in mineral oil, 1.20 g, 30.0 mmol) in dimethylsulfoxide (19 mL) was added trimethylsulfoxonium iodide (6.89 g, 31.3 mmol) at room temperature, and the mixture was stirred at room temperature for 30 min. To this mixture was added a solution of 4-methoxycyclohexanone (3.53 g, 10.0 mmol, prepared according to Shvily, Ronit et al., *J. Chem. Soc. Perkin Trans.* 2, 1997, 6, 1221) in dimethylsulfoxide (95 mL) dropwise at room temperature, and the mixture was stirred at room temperature for 20 h. Then the mixture was diluted with water (1.0 L), and extracted with diethyl ether (200 mL×6). The combined organic layers were dried over magnesium sulfate, and concentrated in vacuo. The residue was chromatographed on a column of silica gel eluting n-hexane/ethyl acetate (v/v=15/1~10/1) to give 338 mg (9%, cis) and 204 mg (5%, trans) of the title compound as colorless oil respectively.

(cis)

$^1$H-NMR (CDCl$_3$) δ: 3.37 (3H, s), 3.36-3.28 (1H, m), 2.65 (2H, s), 1.95-1.88 (2H, m), 1.81-1.55 (6H, m).

(trans)

$^1$H-NMR (CDCl$_3$) δ: 3.46-3.40 (1H, m), 3.36 (3H, s), 2.64 (2H, s), 1.99-1.91 (2H, m), 1.85-1.67 (4H, m), 1.48-1.39 (2H, m).

8(2) 5-Chloro-N-({1-[(cis-1-hydroxy-4-methoxycyclohexyl)methyl]piperidin-4-yl}methyl)-1-isopropyl-6-methyl-2-oxo-1,2-dihydropyridine-3-carboxamide

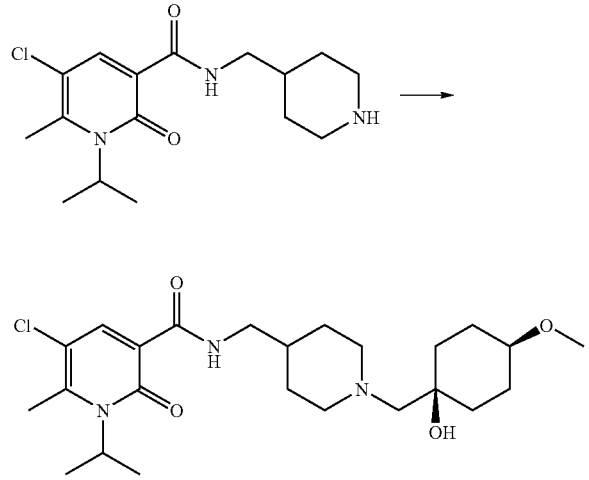

A mixture of 5-chloro-1-isopropyl-6-methyl-2-oxo-N-(piperidin-4-ylmethyl)-1,2-dihydropyridine-3-carboxamide as prepared in Example 6(2) (326 mg, 1.0 mmol) and (3s,6s)-6-methoxy-1-oxaspiro[2.5]octane (cis) as prepared in Example 8(1) (204 mg, 1.43 mmol) in methanol (3 mL) was stirred at room temperature for 3 days, and then the solvent was removed in vacuo. The residue was chromatographed on a column of silica gel eluting with dichloromethane/methanol (v/v=20/1~10/1) to give 435 mg (93%) of the title compound as a white solid.

MS (ESI) m/z: 468 (M+H)$^+$, 466 (M−H)$^−$.

m.p.: 165° C. (decomposition).

IR (KBr) ν: 3481, 2912, 2804, 1670, 1537, 1448, 1375, 1350, 1288, 1229, 1171, 1105, 1055, 968, 949, 932, 887, 800, 708 cm$^{-1}$.

$^1$H-NMR (CDCl$_3$) δ: 9.79 (1H, br.), 8.42 (1H, s), 4.69 (1H, br.), 3.35 (3H, s), 3.31 (2H, t, J=6.2 Hz), 3.16-3.06 (1H, m), 2.89-2.85 (2H, m), 2.59 (3H, s), 2.36-2.27 (2H, m), 2.26 (2H, s), 1.86-1.55 (9H, m), 1.64 (6H, d, J=6.8 Hz), 1.40-1.17 (4H, m). A signal due to O$\underline{H}$ was not observed.

Anal. Calcd. for C$_{24}$H$_{38}$N$_3$O$_4$Cl: C, 61.59; H, 8.18; N, 8.98. Found: C, 61.28; H, 8.15; N, 8.87.

Example 9

5-CHLORO-N-({1-[(TRANS-1-HYDROXY-4-METHOXYCYCLOHEXYL)METHYL]PIPERIDIN-4-YL}METHYL)-1-ISOPROPYL-6-METHYL-2-OXO-1,2-DIHYDROPYRIDINE-3-CARBOXAMIDE

A mixture of 5-chloro-1-isopropyl-6-methyl-2-oxo-N-(piperidin-4-ylmethyl)-1,2-dihydropyridine-3-carboxamide as prepared in Example 6(2) (326 mg, 1.0 mmol) and

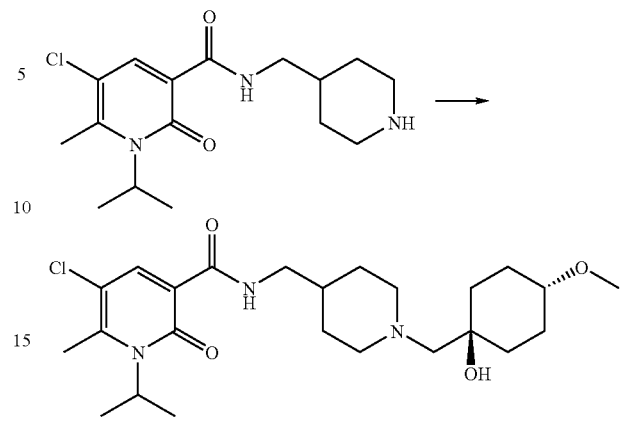

(3R,6R)-6-methoxy-1-oxaspiro[2.5]octane (trans) as prepared in Example 8(1) (204 mg, 1.43 mmol) in methanol (3 mL) was stirred at room temperature for 3 days, and then the solvent was removed in vacuo. The residue was chromatographed on a column of silica gel eluting with dichloromethane/methanol (v/v=20/1~10/1) to give 425 mg (91%) of the title compound as a white solid.

MS (ESI) m/z: 468 (M+H)$^+$, 466 (M−H)$^−$.

m.p.: 175° C. (decomposition).

IR (KBr) ν: 3217, 2924, 1672, 1618, 1541, 1439, 1375, 1350, 1202, 1169, 1151, 1090, 1051, 982, 972, 945, 891, 799, 706 cm$^{-1}$.

$^1$H-NMR (CDCl$_3$) δ: 9.79 (1H, br.), 8.42 (1H, s), 4.68 (1H, br.), 3.42-3.36 (1H, m), 3.33-3.29 (5H, m), 2.89-2.85 (2H, m), 2.59 (3H, s), 2.36-2.28 (4H, m), 1.90-1.51 (9H, m), 1.64 (6H, d, J=7.0 Hz), 1.42-1.26 (4H, m). A signal due to O$\underline{H}$ was not observed.

Anal. Calcd. for C$_{24}$H$_{38}$N$_3$O$_4$Cl.0.3H$_2$O: C, 60.89; H, 8.22; N, 8.88. Found: C, 60.57; H, 8.27; N, 8.80.

Example 10

5-CHLORO-N-({1-[(TRANS-1,4-DIHYDROXY-4-METHYLCYCLOHEXYL)METHYL]PIPERIDIN-4-YL}METHYL)-1-ISOPROPYL-6-METHYL-2-OXO-1,2-DIHYDROPYRIDINE-3-CARBOXAMIDE

10(1) 1-{[(3r,6r)-6-Hydroxy-1-oxaspiro[2.5]oct-6-yl]methyl}piperidine-4-carboxamide

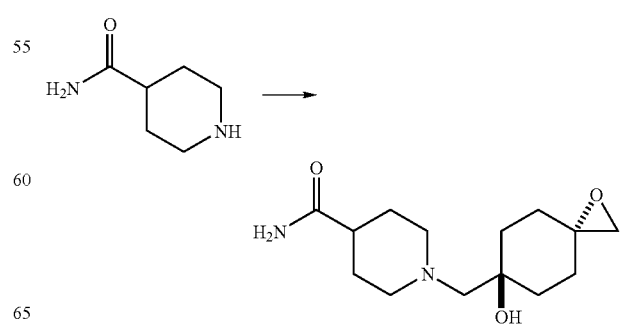

A mixture of isonipecotamide (128 mg, 1.0 mmol) and (3R,6R)-1,7-dioxadispiro[2.2.2.2]decane (280 mg, 2.0 mmol, prepared according to Alfredo G. Causa et al., *J. Org. Chem.*, 1973, 7, 1385) in methanol (10 mL) was stirred at room temperature for 18 h, and then the solvent was removed in vacuo. The residue was dispersed in dichloromethane (10 mL) and the resulting suspension was filtered washing with dichloromethane (10 mL). The filtered solid was collected and dried in vacuo to give 196 mg (73%) of the title compound as a white solid.

MS (ESI) m/z: 269 (M+H)$^+$.

$^1$H-NMR (DMSO-$d_6$) δ: 7.19 (1H, br.), 6.69 (1H, br.), 2.93-2.88 (2H, m), 2.56 (2H, s), 2.22 (2H, s), 2.16-1.93 (4H, m), 1.61-1.48 (8H, m), 1.27-1.24 (1H, m), 1.05-1.00 (2H, m). A signal due to O$\underline{H}$ was not observed.

10(2) trans 1-{[4-(Aminomethyl)piperidin-1-yl]methyl}-4 methylcyclohexane 1,4-diol

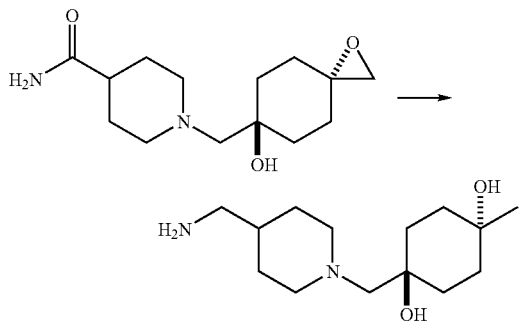

To a stirred suspension of 1 {[(3R,6R)-6-hydroxy-1-oxaspiro[2.5]oct-6-yl]methyl}piperidine-4-carboxamide as prepared in 10(1) (196 mg, 0.73 mmol) in tetrahydrofuran (25 mL) was added lithium aluminum hydride (83 mg, 2.19 mmol) at 0° C., and the mixture was stirred at room temperature for 5 h then refluxed for 20 h. The mixture was quenched with water (0.1 mL) at 0° C., and stirred at room temperature for 20 rain. Then 15% sodium hydroxide aqueous solution (0.1 mL) was added, and stirred at room temperature for 20 min. Finally, water (0.3 mL) was added, and stirred at room temperature for 20 min. The mixture was filtered through Celite pad washing with tetrahydrofuran (25 mL). The filtrate was concentrated in to give 220 mg (99%) of the title compound as a colorless oil.

MS (ESI) m/z: 257 (M+H)$^+$.

10(3) 5-chloro-N-({1-[(trans 1,4-dihydroxy-4-methylcyclohexyl)methyl]piperidin-4-yl}methyl)-1-isopropyl-6-methyl-2-oxo-1,2-dihydropyridine-3-carboxamide

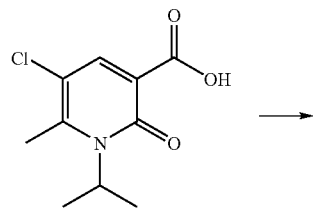

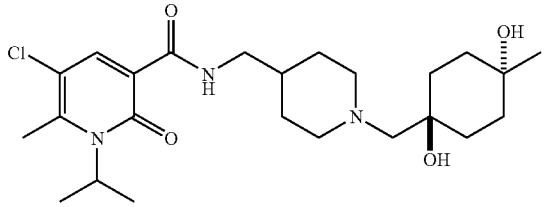

To a solution of 5-chloro-1-isopropyl-6-methyl-2-oxo-1,2-dihydropyridine-3-carboxylic acid as prepared in 1(7) (168 mg, 0.73 mmol) in dichloromethane (5 mL) were added oxalyl chloride (278 mg, 2.19 mmol) and a drop of N,N-dimethylformamide at room temperature, and the mixture was stirred at room temperature for 2 h. The solvent and excess amounts of oxalyl chloride were removed in vacuo. The residue was dissolved in dichloromethane (3 mL). To the resulting solution were added trans-1-{[4-(aminomethyl)piperidin-1-yl]methyl}-4-methylcyclohexane-1,4-diol as prepared in 10(2) (187 mg, 0.73 mmol), N,N-diisopropylethylamine (94 mg, 0.73 mmol) at room temperature, and the mixture was stirred at room temperature for 18 h. Then, the mixture was quenched with saturated sodium hydrogencarbonate aqueous solution (50 mL), and extracted with dichloromethane (50 mL×3). The combined organic layers were dried over magnesium sulfate and concentrated in vacuo. The residue was purified with plate TLC eluting with dichloromethane/methanol/25% ammonium hydroxide (v/v/v=10/1/0.2) to give 69 mg (20%) of the title compound as a white solid.

MS (ESI) m/z: 468 (M+H)$^+$, 466 (M-H)$^-$.

m.p.: 189° C. (decomposition).

IR (KBr) ν: 3431, 3211, 2918, 1666, 1537, 1448, 1308, 1290, 1231, 1169, 1113, 1082, 1045, 997, 957, 903, 881, 800, 710 cm$^{-1}$.

$^1$H-NMR (CDCl$_3$) δ: 9.80 (1H, br.), 8.42 (1H, s), 4.68 (1H, br.), 3.31 (2H, t, J=6.4 Hz), 2.91-2.87 (2H, m), 2.60 (3H, s), 2.37-2.30 (4H, m), 1.85-1.23 (16H, m), 1.64 (6H, d, J=6.8 Hz).

Two signals due to O$\underline{H}$ were not observed.

Anal. Calcd. for $C_{24}H_{38}N_3O_4Cl.0.2H_2O$: C, 61.12; H, 8.21; N, 8.91. Found: C, 61.06; H, 8.26; N, 8.53.

The invention claimed is:

1. A compound of the formula (I):

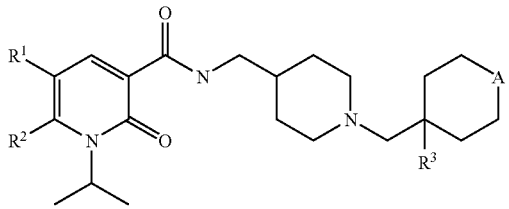

wherein
R$^1$ is alkyl having 1 to 4 carbons or halogen;
R$^2$ is alkyl having 1 to 4 carbons;
R$^3$ is hydrogen or hydroxy; and
A is oxygen;
or a pharmaceutically acceptable salt thereof.

2. The compound of claim 1, wherein R$^1$ is halogen.

3. The compound of claim 1, wherein R$^2$ is alkyl having 1 to 2 carbons.

4. The compound of claim 2, wherein R$^2$ is alkyl having 1 to 2 carbons.

5. The compound of claim 1, wherein R$^3$ is hydroxy.

6. The compound of claim 2, wherein R$^3$ is hydroxy.

7. The compound of claim 4, wherein $R^3$ is hydroxy.

8. A compound selected from:
- 5-chloro-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide;
- 5-chloro-6-ethyl-N-({1-[(4-hydroxytetrahydro-2H-pyran-4-yl)methyl]piperidin-4-yl}methyl)-1-isopropyl-2-oxo-1,2-dihydropyridine-3-carboxamide;
- N-({1-[(4-hydroxytetrahydro-2H-pyran-4-yl)methyl]piperidin-4-yl}methyl)-1-isopropyl-5,6-dimethyl-2-oxo-1,2-dihydropyridine-3-carboxamide;
- 5-bromo-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide; or
- 5-fluoro-N-({1-[(4-hydroxytetrahydro-2H-pyran-4-yl)methyl]piperidin-4-yl}methyl)-1-isopropyl-6-methyl-2-oxo-1,2-dihydropyridine-3-carboxamide;

or a pharmaceutically acceptable salt thereof.

9. A pharmaceutical composition comprising a compound of claim 1 or a pharmaceutically acceptable salt thereof together with at least one pharmaceutically acceptable carrier.

10. A method for treating gastroesophageal reflux disease, gastric motility disorder, non-ulcer dyspepsia, functional dyspepsia, irritable bowel syndrome (IBS), dyspepsia, esophagitis, and, nausea, comprising administering to a mammal in need of such treatment a therapeutically effective mount of a compound according to claim 1 or a pharmaceutically acceptable salt thereof.

11. A method for treating gastroesophageal reflux disease comprising administering to a mammal in need of such treatment a therapeutically effective amount of a compound according to claim 1 or a pharmaceutically acceptable salt thereof.

* * * * *